United States Patent [19]

Grauert et al.

[11] Patent Number: 5,196,454
[45] Date of Patent: Mar. 23, 1993

[54] METHOD OF TREATING DISORDERS OF THE DOPAMINERGIC SYSTEMS USING 2,5-DIAMINOTETRALINES

[75] Inventors: Matthias Grauert; Herbert Merz, both of Ingelheim am Rhein; Joachim Mierau, Mainz; Gunter Schingnitz, Bad Kreuznach; Claus Schneider, Eppelheim, all of Fed. Rep. of Germany

[73] Assignee: Boehringer Ingelheim KG, Ingelheim am Rhein, Fed. Rep. of Germany

[21] Appl. No.: 539,093

[22] Filed: Jun. 15, 1990

[30] Foreign Application Priority Data

Jun. 15, 1989 [DE] Fed. Rep. of Germany ....... 3919624

[51] Int. Cl.$^5$ .................. A61K 31/135; C07C 211/60
[52] U.S. Cl. .................................. 514/654; 514/231.2;
514/247; 514/249; 514/255; 514/256; 514/259;
514/307; 514/311; 514/319; 514/357; 514/365;
514/367; 514/372; 514/374; 514/375; 514/378;
514/394; 514/400; 514/406; 514/412; 514/438;
514/471; 544/162; 544/224; 544/242; 544/283;
544/336; 544/353; 546/149; 546/176; 546/206;
546/329; 548/152; 548/202; 548/214; 548/217;
548/235; 548/247; 548/469, 549/74; 549/492;
560/28; 564/50; 564/163; 564/167; 564/184;
564/222; 564/306; 564/374; 564/383; 564/389;
564/391; 564/428; 548/305.4, 306.1, 304.7,
305.1; 548/309.4, 312.1, 312.4, 312.7; 548/315.1,
315.4, 334.1, 335.5; 548/364.7, 365.1, 365.7,
374.1

[58] Field of Search ................. 564/374, 383, 428, 50,
564/163, 167, 184, 222, 306, 389, 391; 514/654,
657, 510, 597, 617, 629, 655; 560/28

[56] References Cited

U.S. PATENT DOCUMENTS

| | | | |
|---|---|---|---|
| 3,930,022 | 12/1975 | Hauck et al. | 564/374 |
| 4,101,677 | 7/1978 | Dunnigan et al. | 514/657 |
| 4,442,126 | 4/1984 | Beeley et al. | 514/657 |
| 4,873,262 | 10/1989 | Junge et al. | 514/657 |
| 4,968,679 | 11/1990 | Junge et al. | 564/163 |

FOREIGN PATENT DOCUMENTS 0041488 12/1981 European Pat. Off. ............ 514/654

OTHER PUBLICATIONS

Cowen, R., "Receptor Encounters–Untangling the Threads of the Serotonin System", Science News, vol. 136, 248–252 (Oct. 1989).

*Primary Examiner*—Richard L. Raymond
*Attorney, Agent, or Firm*—David E. Frankhouser; Daniel Reitenbach; Mary-Ellen M. Timbers

[57] ABSTRACT

The invention relates to novel 2,5-diaminotetralines of the formula:

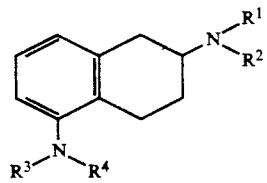

wherein R1, R2, R3 and R4 are defined herein, processes for preparing them and their use in pharmaceutical compositions. The novel 2,5-diaminotetralines are useful in treating diseases caused by disorders of the dopaminergic systems.

7 Claims, No Drawings

METHOD OF TREATING DISORDERS OF THE DOPAMINERGIC SYSTEMS USING 2,5-DIAMINOTETRALINES

1. DEFINITIONS

The invention relates to new 2,5-diaminotetralines (2,5-diamino-1,2,3,4-tetrahydronaphthalines), the preparation thereof and their use as pharmaceutical compositions. The 2,5-diaminotetralines according to the invention correspond to general formula 1

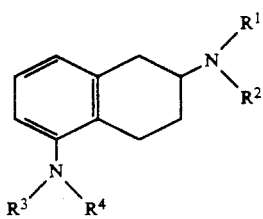

wherein $R^1$ represents hydrogen, $C_{1-12}$ alkyl, $C_{3-12}$ alkenyl, $C_{3-12}$ alkynyl, $-(CH_2)_a$-cycloalkyl, aralkyl and a represents one of the numbers 1,2,3,4,5,6,7,8,9,10,11,12;

$R^2$ represents $C_{1-12}$ alkyl, $C_{3-12}$ alkenyl, $C_{3-12}$ alkynyl, $-(CH_2)_b$-cycloalkyl,

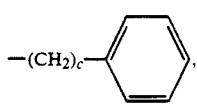

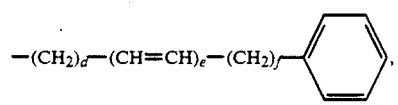

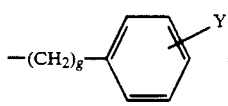

$-(CH_2)_h$heteroaryl, acyl and b represents one of the numbers 1,2,3,4,5,6,7,8,9,10,11,12, c represents one of the numbers 1,2,3,4,5,6,7,8,9,10,11,12, d represents one of the numbers 1,2,3,4,5,6, e represents one of the numbers 1,2,3, f represents one of the numbers 0,1,2,3,4, g represents one of the numbers 1,2,3,4,5,6, h represents one of the numbers 1,2,3,4,5,6,7,8,9,10,11,12,13,14,15,16,17,18,19,20, and Y represents $C_{1-12}$ alkyl, halogen, alkoxy or hydroxy;

$R^3$ represents hydrogen, $C_{1-12}$ alkyl, $C_{3-12}$ alkenyl, $C_{3-12}$ alkynyl, $-(CH_2)_i$-cycloalkyl, aralkyl, formyl, acyl, alkylcarbonyl, alkyloxycarbonyl,

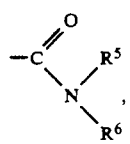

$R^5$ represents alkyl, $R^6$ represents alkyl, $R^5$ and $R^6$ together with the nitrogen atom may also represent a heterocyclic group which may also contain another heteroatom (such as nitrogen, oxygen or sulphur), for example a morpholine, piperidine or piperazine ring and i represents one of the numbers 1,2,3,4,5,6,7,8,9,10,11,12;

$R^4$ represents hydrogen or $C_{1-12}$ alkyl.

Preferred compounds are the compounds of general formula 1 wherein $R^1$ represents hydrogen, $C_{1-6}$ alkyl, $C_{3-6}$ alkenyl, $C_{3-6}$ alkynyl, $-(CH_2)_a$-cycloalkyl, aralkyl carbon atoms in the aliphatic part and a represents one of the numbers 1,2,3,4,5,6;

$R^2$ represents $C_{1-6}$ alkyl, $C_{3-6}$ alkenyl, $C_{3-6}$ alkynyl, $-(CH_2)_b$-cycloalkyl,

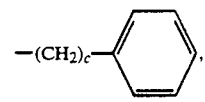

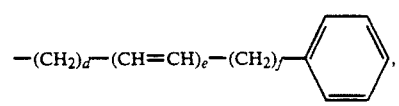

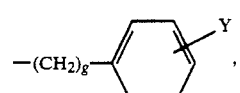

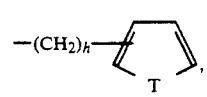

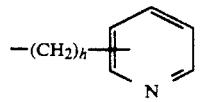

acyl and b represents one of the numbers 1,2,3,4,5,6, c represents one of the numbers 1,2,3,4,5,6,7, 8,9,10, d represents one of the numbers 1,2,3, e represents one of the numbers 1,2, f represents one of the numbers 0,1,2, g represents one of the numbers 1,2,3,4, h represents one of the numbers 1,2,3,4,5,6,7, 8,9,10,12,13,14 and Y represents $C_{1-6}$ alkyl, halogen, lower alkoxy or hydroxy, T represents oxygen, sulphur or nitrogen;

$R^3$ represents hydrogen, $C_{1-6}$ alkyl, $C_{3-6}$ alkenyl, $C_{3-6}$ alkynyl, $-(CH_2)_i$-cycloalkyl, phenylalkyl, formyl, aryl, alkylcarbonyl, alkoxycarbonyl,

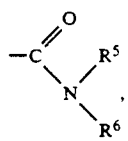

$R^5$ represents lower alkyl,
$R^6$ represents lower alkyl,
$R^5$ and $R^6$ together with the nitrogen atom may also form a heterocyclic group which may also contain a further heteroatom (such as nitrogen, oxygen or sulphur), for example a morpholine, piperidine or piperazine ring and i represents one of the numbers 1,2,3,4,5,6;

$R^4$ represents hydrogen or lower alkyl.

Particularly preferred compounds are those of general formula I wherein $R^1$ represents hydrogen, methyl, ethyl, propyl, allyl, propargyl, cyclopropylmethyl, benzyl;

$R^2$ represents methyl, ethyl, propyl, allyl, propargyl, cyclopropylmethyl,

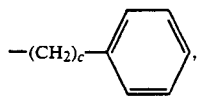

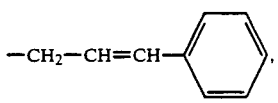

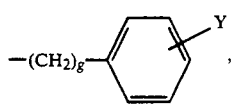

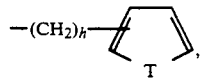

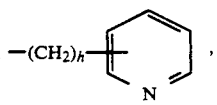

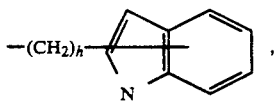

acyl and c represents one of the numbers 1,2,3,4,5,6,7,8,9,
g represents one of the numbers 2,3,
h represents one of the numbers 1,2,3,4,5,6,7,8,9, 10,11,12,
Y represents methyl, fluorine, chlorine, bromine, methoxy, hydroxy,
T represents oxygen or sulphur;
$R^3$ represents hydrogen, methyl, ethyl, propyl, allyl, propargyl, cyclopropylmethyl, benzyl, phenylethyl, phenylpropyl, formyl, acyl, methylcarbonyl, ethylcarbonyl, trifluoromethylcarbonyl, methoxycarbonyl, aminocarbonyl;
$R^4$ represents hydrogen, methyl, ethyl, n-propyl and isopropyl.

The 2,5-diaminotetralines according to the invention (2,5-diamino-1,2,3,4-tetrahydronaphthalines) contain at least one carbon atom with a centre of asymmetry and, depending on the pattern of substitution, may also have a plurality of centres of asymmetry and may therefore exist in various stereochemical forms.

Examples include the following isomers of the substituted 2,5-diaminotetralines of general formula 1a and 1b

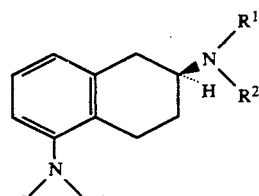

1a

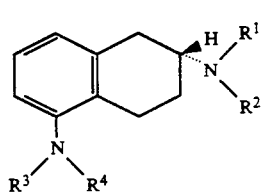

1b

The invention relates to the individual isomers, mixtures thereof and the corresponding physiologically acceptable acid addition salts with organic or inorganic acids. Preferred salts include, for example, salts obtained with hydrochloric, hydrobromic, sulphuric, phosphoric, methanesulphonic, ethanesulphonic, toluenesulphonic, benzenesulphonic, lactic, malonic, succinic, maleic, fumaric, malic, tartaric, citric or benzoic acid.

Unless otherwise stated, the general definitions are used as follows:

Alkyl generally represents a branched or unbranched hydrocarbon radical with 1 to 12 carbon atoms which may optionally be substituted with a halogen atom or several halogen atoms, preferably fluorine, which may be identical or different, the lower alkyl groups being preferred. Lower alkyl generally means a branched or unbranched hydrocarbon group with 1 to about 6 carbon atoms. Examples include methyl, ethyl, propyl, isopropyl, butyl, isobutyl, pentyl, isopentyl, neopentyl, hexyl, isohexyl, heptyl, isoheptyl, octyl and isooctyl.

Alkenyl generally represents a straight-chained or branched hydrocarbon radical with 3 to 12 carbon atoms and with one or more, preferably one or two double bonds, which may optionally be substituted with a halogen atom or several halogen atoms, preferably fluorine, which may be identical or different. A lower alkenyl group with 3 to about 6 carbon atoms and one or two double bonds is preferred. An alkenyl group with 3 or 4 carbon atoms and one double bond is particularly preferred. Examples of this are allyl, propenyl, isopropenyl, pentenyl, isopentenyl, hexenyl, isohexenyl, heptenyl, isoheptenyl, octenyl and isooctenyl.

Alkynyl generally means a straight-chained or branched hydrocarbon group with 3 to 12 carbon atoms and with one or more, preferably one or two triple bonds. A lower alkynyl group with 3 to about 6 carbon atoms and one or two triple bonds is preferred, optionally substituted with a halogen atom or several halogen atoms which may be identical or different. An alkynyl group with 3 or 4 carbon atoms and one triple bond is particularly preferred. Examples include propargyl and but-2-ynyl.

Cycloalkyl generally represents a saturated or unsaturated cyclic hydrocarbon group with 3 to 9 carbon atoms which may optionally be substituted by a halogen atom or several halogen atoms which may be identical or different. Cyclic hydrocarbons with 3 to 6 carbon atoms are preferred. Examples include cyclopropyl, cyclobutyl, cyclopentyl, cyclopentenyl, cyclohexyl, cyclohexenyl, cycloheptyl, cycloheptenyl, cycloheptadienyl and cyclooctyl, cyclooctenyl, cyclooctadienyl, cyclononynyl.

Aralkyl generally represents an aryl group with 7 to 14 carbon atoms bound via an alkylene chain, wherein the aromatic group may be substituted by one or more lower alkyl groups, alkoxy groups, alkoxycarbonyl groups, hydroxy groups, cyano groups, nitro groups, amino groups and/or one or more halogen atoms (which may be identical or different). Aralkyl groups with 1 to 6 carbon atoms in the aliphatic part and 6 to 10 carbon atoms in the aromatic part are preferred. The preferred aralkyl groups are: benzyl, naphthylmethyl, phenethyl and phenylpropyl.

Alkoxy generally represents a straight-chained or branched hydrocarbon group with 1 to 12 carbon atoms bound via an oxygen atom. A lower alkoxy group with from 1 to about 6 carbon atoms is preferred. An alkoxy group with 1 to 4 carbon atoms is particularly preferred. Examples include methoxy, ethoxy, propoxy, isopropoxy, butoxy, isobutoxy, tert.-butoxy, pentoxy, isopentoxy, hexoxy, isohexoxy, heptoxy, isoheptoxy, octoxy or isooctoxy.

Acyl generally represents benzoyl or alkylcarbonyl groups such as straight-chained or branched lower alkyl groups with 1 to about 6 carbon atoms which are bound via a carbonyl group, whilst the alkyl group may optionally be substituted by one or more halogen atoms which may be identical or different. Alkyl groups with up to 4 carbon atoms are preferred. Examples include: acetyl, trifluoroacetyl, ethylcarbonyl, propylcarbonyl, isopropylcarbonyl, butylcarbonyl and isobutylcarbonyl.

Alkoxycarbonyl may be represented, for example, by the formula

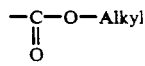

Alkyl here represents a straight-chained or branched hydrocarbon group with 1 to 12 carbon atoms. A lower alkoxycarbonyl group with 1 to 6 carbon atoms is preferred. An alkoxycarbonyl group with 1 to 4 carbon atoms in the alkyl group is particularly preferred. The following alkoxycarbonyl groups may be mentioned by way of example: methoxycarbonyl, ethoxycarbonyl, propoxycarbonyl, isopropoxycarbonyl, butoxycarbonyl or isobutoxycarbonyl.

Heteroaryl within the scope of the above definitions generally represents a 5- to 6-membered ring which may contain oxygen, sulphur and/or nitrogen as heteroatoms and which may have a further aromatic ring fused thereon. 5- and 6-membered aromatic rings which contain an oxygen, a sulphur and/or up to two nitrogen atoms and which are optionally benzofused are preferred. Examples of particular heteroaryl groups include thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl and indolyl.

Unless otherwise stated, halogen represents fluorine, chlorine or bromine and, to a lesser extent, iodine.

2. Pharmacological properties

The new compounds of general formula 1 and the pharmacologically acceptable acid addition salts thereof embody centrally active dopamine agonists. Depending on their individual chemical structures they exhibit different selectivities for morphologically and/or functionally differentiated dopamine receptors and various activity profiles resulting from them. They can therefore be used therapeutically in the treatment of various diseases caused by disorders of the dopaminergic systems, e.g. for the treatment of schizophrenia, Parkinson's disease, prolactin hyperfunction and high blood pressure.

It has proved particularly valuable to use compounds or hydrochlorides thereof of general formula 1 wherein $R^1$ and $R^2$ independently of each other represent hydrogen (with the exception of $R^2$), methyl, ethyl, propyl, phenyl, benzyl, phenethyl, phenylpropyl or a heteroaryl group bound via an alkyl chain with 1 to 5 carbon atoms, with furan, thiophene, pyridine and indole being preferred heterocycles and $R^3$ representing hydrogen, methyl or acetyl and $R^4$ representing hydrogen.

The following compounds have proved particularly valuable as enantiomerically pure substances and also in the form of mixtures or racemates or the pharmacologically active salts thereof:

A: (±)-5-amino-2-(3-phenylpropyl-amino)-tetraline
B: (±)-5-amino-2-[N-(3-phenylpropyl)-N-n-propylamino]-tetraline
C: (±)-5-amino-2-(4-phenylbutyl-amino)-tetraline
D: (±)-5-amino-2-[N-(4-phenylbutyl)-N-n-propyl-amino]-tetraline 2.1 Determining the inhibition of dopamine synthesis The procedure followed is that of J. R. Walters and R. H. Roth [Naunyn—Schmiedeberg's Arch. Pharmacol. 296, (1976) 5]: five animals are each given 10 mg/kg s.c. of the test substance. After 5 minutes they are given 750 mg/kg i.p. of γ-butyrolactone in order to rule out the influence of post-synaptic feedback loops on the dopamine synthesis rate by blocking the pre-synaptic impulse connection. The administration of γ-butyrolactone results in a substantial increase in the synthesis of DOPA or dopamine. In order to inhibit the decarboxylation of DOPA, 200 mg/kg of 3-hydroxybenzylhydrazine hydrochloride are administered by intraperitoneal route after a further 5 minutes. 40 minutes after the substance has been administered the animals are killed and the Corpus striatum is dissected out. The DOPA-content is measured using HPLC with electrochemical detection (standard: dihydroxybenzylamine).

The percentage inhibition, brought about by the test substance, in the DOPA-accumulation stimulated by γ-butyrolactone is determined by comparison with the control animals treated with 0.9% saline solution.

The results of this test are assembled in the following Table:

| Substance | Dose (mg/kg s.c.) | Inhibition of dopa-accumulation in % compared with the control animals treated with saline |
| --- | --- | --- |
| A | 10 | 45.5 |
| B | 10 | 63.5 |

3. Method of preparation

The compounds of general formula 1 can be prepared by various methods known per se. The methods listed in the reaction plan (page 13) are preferred. The key compounds are 5-amino-2-tetralones (2) which may be prepared for example analogously to the 5-acetylamino compound ((2), —Z=—COCH$_3$) (J. W. Cornforth et al., J. Chem. Soc. 1955, 3348).

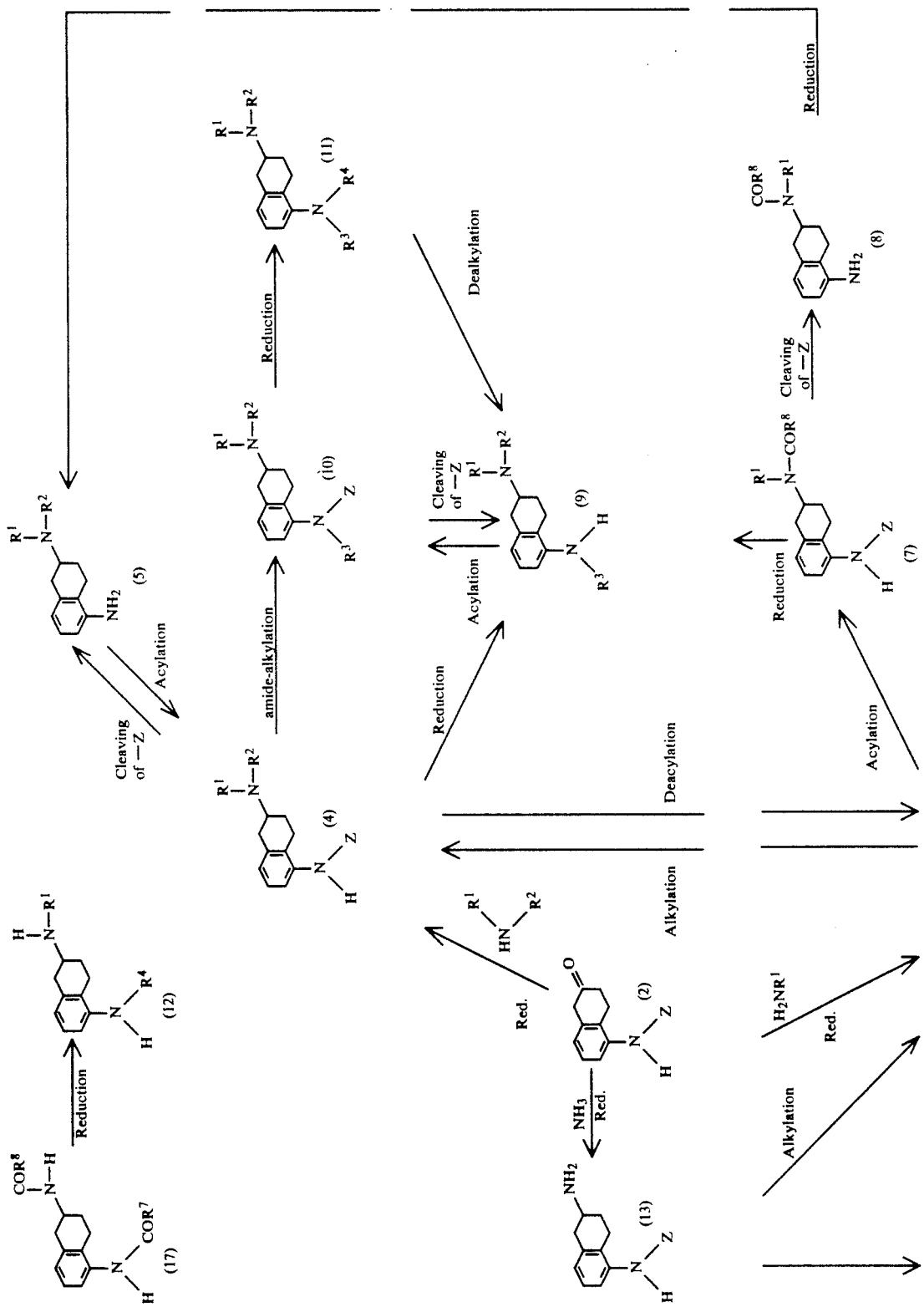

-continued
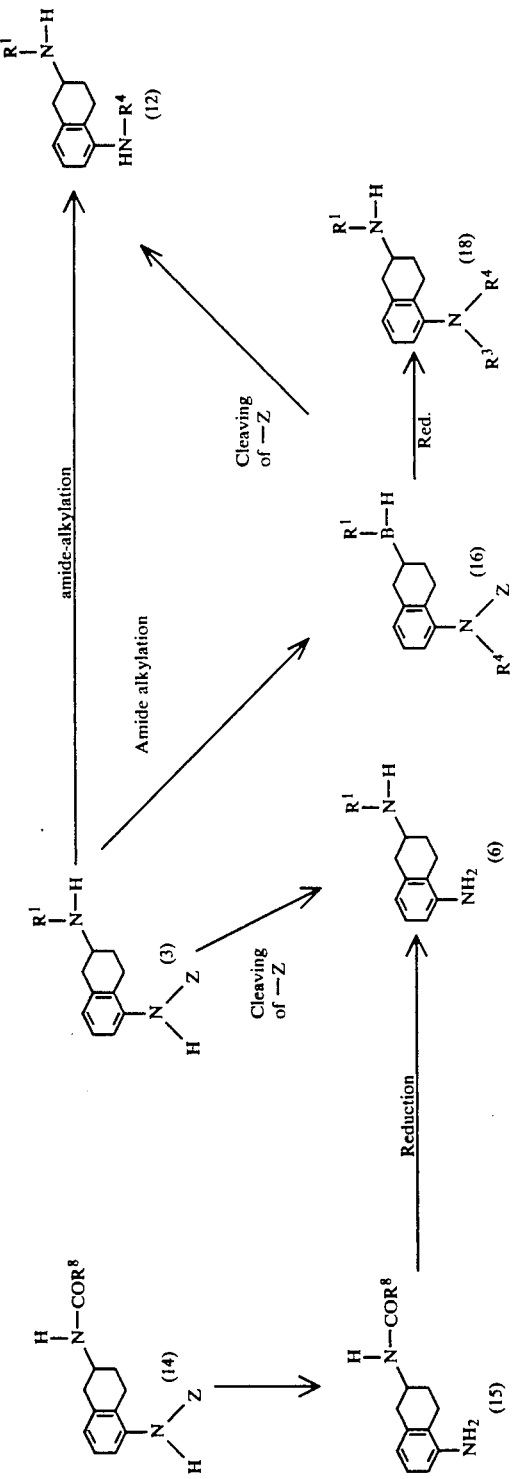

—Z is an acid group which may be retained if it has the meaning acyl given in the general formula 1 for —R³. However, it may also act as a precursor —CO—R⁷ which is converted into one of the substituents —R³ or —R⁴ defined in general formula 1. Finally, it may also have the function of a protective group [T. W. Greene, Protective Groups in Organic Synthesis, John Wiley and Sons, New York 1981], which are split off again in the course of the synthesis of compounds of general formula 1 and are replaced by —H.

The compounds of general formula 1 are chiral substances which may occur in racemic (±)-forms or in enantiomerically pure form as (+)- and (−)-forms. The latter are obtained by stereoselective synthesis, racemate resolution of intermediate products or racemate resolution of racemic substances of general formula 1.

The compounds of general formula 1 are isolated and purified by methods known per se and crystallised as bases or with therapeutically acceptable acids in the form of acid addition compounds.

The individual methods or reaction steps specified in the reaction plan on page 13 are explained hereinafter and supported by the Examples in Section 4.

3.1 2-Amino-5-Z-amino-tetralines (13), (3) and (4) from corresponding 5-Z-amino-2-tetralones (2)

By reductive amination of 5-Z-amino-2-tetralones (2) with ammonia or the relevant primary or secondary amines, the desired compounds (13), (3) or (4) are obtained via intermediate ketimines, Schiff bases or enamines. The intermediate products can be isolated then hydrogenated or reduced to form the end products. It is simpler to carry out both steps in a one-pot process.

The intermediate compounds are formed in suitable solvents, preferably in the presence of a catalyst and an agent which dries the reaction. Suitable solvents include all inert organic solvents which remain unchanged or at least substantially unchanged under the reaction conditions used and do not interfere with the progress of the reaction. These include amides such as dimethylformamide or hexamethyl phosphoric acid triamide or esters such as methyl acetate or ethyl acetate or ethers such as diethylether, tert.-butylmethylether, din-butylether, glycoldimethylether (glyme), diglycolide methylether (diglyme), tetrahydrofuran and dioxan, and preferably alcohols, especially methanol and ethanol. These and other solvents may be used in the form of mixtures. The starting compounds are preferably reacted in solution but may also be brought to reaction in suspension. Suitable catalysts are acids, especially protonic acids. These preferably include inorganic acids such as hydrochloric, phosphoric or sulphuric acid or organic acids with from 1 to 6 carbon atoms which may optionally be substituted by fluorine, chlorine and/or bromine. Examples of these acids are formic, acetic, trifluoroacetic, trichloroacetic or propionic acid. The preferred acids also include sulphonic acids with $C_{1-4}$ alkyl groups or aryl groups which may optionally be substituted by halogens, such as methanesulphonic acid, trifluoromethanesulphonic acid, ethanesulphonic acid, benzenesulphonic acid or toluenesulphonic acid. Hydrochloric and hydrobromic acid are particularly preferred. These acids may be used in catalytic amounts, but it is preferable to use equivalent quantities or an excess. It is advantageous to eliminate the water which forms during the reaction from the equilibrium e.g. by distilling or by the addition of drying agents such as phosphorus pentoxide or preferably molecular sieves. The reaction may be carried out within a wide temperature range which in practice is limited at the lower end by an insufficient reaction speed and at the upper end by the predominance of subsidiary reactions. A favourable range is between 0° and 100° C., preferably between 20° and 50° C. The reaction is usually carried out under normal pressure but it is also possible to work at higher or lower pressures. The reactants are used in equimolar quantities but, depending on the reactants used, it is favourable to have an excess of the amine component, preferably up to a 5-fold excess.

The further reaction of the intermediates is carried out for example by catalytic hydrogenation in suitable solvents, preferably in methanol or ethanol. However, it is also possible to use other solvents such as carboxylic acids, ethers and the like as well as mixtures of solvents. Examples of suitable catalysts are the known hydrogenation catalysts, e.g. those based on palladium, platinum or nickel. For reduction with hydrogen, the reaction is carried out under the reaction conditions known for catalytic hydrogenation, depending on the catalysts, solvents and reactants used in each particular case [K. Harada in Patai, "The Chemistry of the Carbon-Nitrogen Double Bond", Interscience Publishers, London 1970, page 276 and cited literature; P. N. Rylander, Catalytic Hydrogenation over Platinum Metals, Academic Press, New York 1967, page 123; F. Moller and R. Schroter in Houben-Weyl, Methoden der organischen Chemie, Volume XI/1, Georg Thieme Verlag, Stuttgart 1957, p. 602; W. S. Emerson, Org. Reactions 4 (1949) 174; E. M. Hancock and A. C. Cope, Org. Synth., Coll. Vol. III (1955) 501; J. C. Robinson and H. R. Snyder, Org. Synth., Coll, Vol. III (1955) 717; D. M. Malcolm and C. R. Noller, Org. Synth., Coll. Vol. IV (1963) 603]. It is particularly preferred to carry out hydrogenation with palladium on charcoal (containing 10% palladium) in methanol. As a rule, hydrogenation can be successfully carried out at normal pressure and ambient temperature. However, these parameters may be varied. Preferably, the pressures used are from 1 to 5 bar and the temperatures used are between 0° and 100° C. and more particularly 20° to 50° C. Alternatively, the intermediate products may also be reduced by other methods. It is preferable to use for this purpose complex hydrides, particularly those of aluminium or boron such as lithium aluminium hydride, sodium borohydride and especially sodium cyanoborohydride. The work is carried out in solvents which are suitable for the hydrides in question, e.g., in the case of lithium aluminium hydride, in ethers such as diethylether or tetrahydrofuran, or in the case of sodium borohydride and sodium cyanoborohydride, in water or alcohols, preferably methanol or ethanol. Reduction with complex hydrides may be catalysed in known manner, especially with protonic acids and preferably with the acids used to form the intermediate products, when the one-pot method is used. The reaction temperature may vary within wide limits, which are defined in practice by an insufficient reaction speed, at the lower end, and by the predominance of subsidiary reactions, at the other end. It is preferred to use temperatures within the range from −50° to +150° C., particularly from 0° to 75° C. As a rule, calculated quantities of the reducing agents are required; however, an excess preferably from 10 to 25% may prove advantageous.

If the substituent —Z has the definition of —R³=acyl, as defined in general formula 1, the end products (3) and (4) obtained correspond to the substances claimed.

If —Z has one of the other meanings defined in general formula 1, there is subsequent conversion of —Z into —R³ or —R⁴ (see the reaction plan on page 13).

3.2 2,5-Diamino-tetralines (5) and (6) by cleaving the corresponding Z-derivatives (4) and (5)

Numerous methods of splitting off Z—where Z has the meanings given for $R^3$ with the exception of acyl—are known from the prior art [T. W. Greene, Protective Groups in Organic Synthesis, John Wiley and Sons, New York 1981 and cited literature].

This cleavage is most easily carried out by acid or alkaline hydrolysis. For acid hydrolysis, it is preferred to use strong inorganic acids such as sulphuric acid, hydrohalic acid such as hydrobromic acid and preferably hydrochloric acid in an aqueous, alcoholic or aqueous-alcoholic solution. Boiling in constantly boiling hydrochloric acid (about 6 N HCl) or in aqueous-ethanolic hydrochloric acid is a particularly simple and well tried method. It is also possible to work at higher or lower temperatures, the range of which is limited in practice by an insufficient reaction speed, at the lower end, and by a predominance of secondary reactions, at the other end.

For alkaline hydrolysis, it is expedient to use strong bases such as alkali or alkaline earth hydroxides, preferably potassium, sodium or barium hydroxide, in an aqueous, alcoholic or aqueous-alcoholic solution. In order to be able to perform the reaction at higher temperatures—which may be necessary under certain circumstances—it may be carried out in glycol or in diglycol. The reaction temperature may vary within wide limits, which are defined by an insufficient reaction speed, at the lower end, and by the predominance of secondary reactions, at the upper end. The temperature is expediently within the range from 0° to 200° C. and preferably between 50° and 150° C.

3.3 2-Alkylamino- and 2-dialkylamino-5-Z-aminotetralines (3) and (4) by alkylation of 2-amino-5-Z-amino-tetralines (13) and (3)

The methods of alkylation which may be used include reductive amination of aldehydes or ketones with the amines (13) or (3).

The same basic method is used as in Section 3.1. For reductive amination of formaldehyde resulting in N-methyl derivatives of (3) or (4), there is also the Leukart-Wallach reaction in which formic acid acts as a reducing agent. The reaction conditions for reductive amination of this kind are known [Autorenkolektiv, Organikum, VEB Deutscher Verlag der Wissenschaften, Berlin 1986 (16th Edition) p. 491; C. Ferri, Reaktionen der organischen Synthese, Georg Thieme Verlag, Stuttgart 1978, p. 133 and cited literature; F. Möller and R. Schröter in Houben-Weyl, Methoden der organischen Chemie, Volume XI/1, Georg Thieme Verlag, Stuttgart 1957, p. 648].

Alternatively, the primary or secondary 2-amino compounds (13) and (3) are reacted with alkylating agents $R^1X$ or $R^2X$. X represents a leaving group which leaves as an anion $X^-$, such as for example X=Cl, Br, I, O—SO₂—OR, O—SO₂—CH₃, O—SO₂—C₆H₅ or O—SO—C₆H₄—CH₃. The alkylating agent is used in calculated quantities or in an excess, preferably from 10 to 25%, and the reaction is expediently carried out in a suitable solvent or mixture of solvents. Examples of suitable solvents are alcohols, ethers or halogenated, preferably chlorinated, hydrocarbons. Methanol, ethanol, tetrahydrofuran and dimethylformamide are preferred. Mixtures of dimethylformamide and tetrahydrofuran have proved particularly suitable. In order to achieve complete reaction, it is generally necessary to add an acid binding agent such as potassium carbonate or potassium hydrogen carbonate, sodium carbonate, lithium carbonate, calcium carbonate, and preferably sodium hydrogen carbonate. The reaction temperature may be varied within wide limits which are defined in practice by an insufficient reaction speed, at the lower end, and a predominance of secondary reaction, at the upper end. The temperatures used in practice range between 0° and 200° C., preferably between 50° and 150° C.

If the substituent —Z has the definition of —R³=acyl, as defined for general formula 1, the compounds (3) and (4) obtained correspond to the substances claimed in general formula 1. If —Z has one of the other meanings given under 3, there will be a subsequent conversion of —Z into —R³ or —R⁴ (see the reaction plan on p. 13).

3.4 2-Alkylamino-5-Z-amino-tetralines (3) by dealkylation of 2-dialkylamino-5-Z-amino-tetralines (4)

Tertiary amides can be dealkylated to secondary amines by various methods. Demethylation and debenzylation are of particular preparative value.

For demethylation, numerous reagents are known, of which bromocyanogen, phosgene, chloroformic acid esters and related substances are of particular importance in laboratory practice. The manner in which the reactions are carried out will depend on the nature of the demethylating agent.

Dealkylation in the form of catalytic debenzylation is of considerable practical value [see also T. W. Greene, Protective Groups in Organic Synthesis, John Wiley and Sons, New York 1981 and literature cited therein]. The work is expediently done in solvents such as water, alcohols, acetic acid or mixtures thereof. However, other solvents are also suitable. Typical debenzylation catalysts are used, based on palladium, platinum or nickel, for example. As a rule, the reaction is carried out at ambient temperature under normal pressure. However, in certain circumstances, somewhat higher temperatures and pressures may have a favourable effect on the course of the reaction. The temperature may be up to 100° C. and the pressure up to 10 bar, but generally pressures of 20° to 50° C. and pressures of 1 to 5 bar are preferred.

If, in the dealkylation product (3), the substituent —Z has the meaning —R³=acyl as defined for general formula 1, these products will correspond to the substances claimed in general formula 1. If on the other hand —Z has one of the other meanings given for R³ or R⁴, there will be subsequent conversion of —Z into —R³ or —R⁴ (see the reaction plan on page 13).

3.5 5-Amino-(2-alkylamino- and 2-dialkylamino)tetralines (6) and (5) by reduction of 2-acylamino precursors (15) and (8)

The starting compounds (15) and (8) may be prepared as follows, for example (see the reaction plan on page 13): 2-amino-5-Z-amino-tetralines (13) and (3), obtained by the method described in 3.1, are modified at the 2-amino-nitrogen to form corresponding 2-acylamino derivatives (14) and (7), respectively. After selective cleavage of —Z, the latter yield the compounds (15) and (8). In these starting compounds (15) and (8), the acyl groups —COR$^8$ at the 2-amino function are such that the N-substituents —R$^1$ or —R$^2$ obtained therefrom by reduction correspond to the definition given in general formula 1.

The reaction of compounds (15) and (8) to obtain the corresponding compounds (6) and (5) is carried out by means of reducing agents. These reductions of acid amides are known from the prior art and may be carried out using the method of electrochemical reduction, by reduction with alkali metals or by catalytic reduction [R. Schröter in Houben-Weyl, Methoden der organischen Chemie, Volume XI/1, Georg Thieme Verlag, Stuttgart 1957, p. 574] or with diborane or hydrogen boride derivatives [J. Fuhrhop and G. Penzlin, Organic Synthesis—Concepts—Methods—Starting Materials, published by VCH of Weinheim 1986, p. 90]. Of the methods available for this purpose, reduction with complex hydrides is particularly suitable in practice. Complex hydrides of aluminium and boron are preferred, and lithium aluminium hydride is particularly preferred. The reactions are carried out in suitable inert solvents which will depend on the nature of the hydride. Reactions with lithium aluminium hydride are preferably carried out in ethers, e.g. diethylether, diisopropylether and, particularly, in tetrahydrofuran, optionally in the presence of a catalyst. [N. G. Gaylord, Reduction with Complex Metal Hydrides, Wiley N.Y. 1965; A. Hájos, Complex Hydrides, Elsevier N.Y. 1979; V. Bazant, M. Capka, M. Cerny, V. Chvalovsky, K. Kochloefl, M. Kraus and J. Málek, Tetrahedron Lett. 9 (1968) 3303]. As a rule, it is favourable to use an excess of the hydride over and above the calculated quantity and this excess is between 5 and 100%, preferably between 10 and 50% of the calculated quantity. The reactants are usually combined whilst being cooled with ice and are then heated. The temperatures are variable within wide limits and are limited in practice by an insufficient reaction speed, at the lower end of the range, and by the predominance of secondary reactions, at the upper end of the range.

3.6 2-Alkylamino- and 2-dialkylamino-5-alkylaminotetralines (12) and (9) by reduction of 5-Z-amino precursors (3) and (4)

Compounds (12) and (9) according to the invention are obtained by reduction from compounds (3) and (4) if the substituents —Z are such (—Z=—COR$^7$) that when reacted they are converted into substituents —R$^3$ or —R$^4$ as claimed in general formula 1. Otherwise, the procedure is as specified in the preceding paragraph 3.5.

3.7 5-Z-(N-alkylamino)-2-dialkylamino-tetralines (10) and (16) by amide-alkylation of 5-Z-amino-2-dialkylamino-tetralines (4) and (3)

The starting compounds are the substances (4) and (3) wherein —NH—Z represents an amide group. For selective alkylation on the amide nitrogen, salts of the amide function are expediently used. Suitable salts include, in particular, the alkali metal salt, preferably sodium salts, which are formed, for example, when sodium hydride or sodium amide reacts with compounds (4) and (3). These salts can be isolated before the alkylation step. It is simpler to produce them and alkylate them in situ in suitable solvents. Examples of reaction media which may be used for this purpose include ethers such as glycolide methylether (glyme), diglycolide methylether (diglyme) and preferably tetrahydrofuran or sulphoxides such as dimethylsulphoxide or acid amides, of which dimethylformamide is particularly preferred [G. Spielberger in Houben-Weyl, Methoden der organischen Chemie, Georg Thieme Verlag, Stuttgart 1957, p. 96; W. F. Fone, J. Org. Chem. 14 (1949) 1099; R. A. W. Johnstone, D. W. Payling and C. Thomas, J. Chem. Soc. [C] 1969, 2223].

For alkylation, alkylating agents R$^3$—X are used and the procedure used is as described in Section 3.3. The reaction will take place at ambient temperature but may also be carried out at lower temperatures provided that acceptable reaction speeds are achieved, or at higher temperatures provided that no disruptive secondary reactions occur. A temperature range from —25° to +150° C. is preferred, whilst it is particularly preferable to work at a temperature in the range from 0° to 75° C.

If in the reaction products the substituent —Z in general formula I has the meaning acyl, of the definitions for R$^3$, the reaction products correspond to the substances claimed in general formula 1. If on the other hand —Z has one of the other meanings defined in general formula 1, —Z will be converted into —R$^4$.

3.8 5-Acylamino-2-dialkylamino-tetralines (4) and (10) by acylation of 5-amino-2-dialkylamino-tetralines (5) and (9)

The compounds (5) and (9) according to the invention are reacted by acylation at the aniline nitrogen to form compounds (4) and (10) which also correspond to the substances claimed in general formula 1 if —Z has the definition —R$^3$=acyl.

There are various methods available for such acylations [C. Ferri, Reaktionen der organischen Synthese, Georg Thieme Verlag, Stuttgart 1978, p. 222 ff]. It is advantageous in practice to carry out reactions with typical acylating agents such as carboxylic acid halides, preferably carboxylic acid chlorides, or carboxylic acid anhydrides. The work is done in suitable inert solvents in the presence of acid binding agents. The inert solvents used are generally organic solvents which do not change under the reaction conditions used, such as hydrocarbons, e.g. benzene, toluene, xylene or petroleum fractions, or halohydrocarbons such as methylene chloride, chloroform or carbon tetrachloride or preferably ethers, such as diethylether, glycoldimethylether (glyme), diglycoldimethylether (diglyme) and tetrahydrofuran. However, it is also possible to use the method of Schotten-Baumann in water in the presence of soda or sodium hydroxide solution [B. C. Challis and J. A. Challis in Zabicky (Ed.), The Chemistry of Amides, Interscience, New York, N.Y. 1970 p. 731 ff]. It is advantageous to carry out acylation by the Einhorn variant in pyridine [Autorenkollektiv, Organikum, VEB Deutscher Verlag der Wissenschaften, Berlin, 1988, (17th Edition) p. 407; L. Gattermann and T. Wieland: Die Praxis des organischen Chemikers, Walter de Gruyter, Berlin, 1982, (43rd Edition) p. 673], which on the one hand has good dissolving qualities and on the other hand acts as an acid binding agent. The reaction temperature may vary within wide limits, the lower limit being an insufficient reaction speed and the upper limit being the predominance of secondary reactions. In practice, the work is done at —50° to +150° C. and preferably in the range from 0° to 100° C.

It is also possible to use special methods of acylation, e.g. with carboxylic acids which are reacted at higher temperatures, preferably 150° to 200° C. with compounds (5) or (9) [A. L. J. Beckwith in: Zabicky (Ed.), The Chemistry of Amides, Interscience, New York, N.Y. 1970, p. 105 ff]. A gentler method is to convert the carboxylic acids temporarily into reactive derivatives which can then be reacted under milder conditions, preferably at 0° to 50° C. Dicyclohexylcarbodiimide or carbonyldiimidazole, for example, are suitable for activating carboxylic acids in this way. The intermediate carboxylic acid derivatives can be isolated or they may preferably be formed and then further reacted in situ.

3.9 5-Alkylamino-2-(mono- and dialkyl-)-aminotetralines (12) and (9) by reduction of diamide precursors (17) and (7)

To prepare the diamides (17) and (7), intermediate products (15) and (3) are used as starting materials. The substituents —$COR^7$, —$COR^8$ and —Z are such that they are converted by reduction into the substituents —$R^1$—$R^4$ defined in general formula 1. The conversion of (15) and (3) into the diamides (17) and (7), respectively, is carried out by acylation analogously to the method described in paragraph 3.8. The diamides are reduced analogously to the methods described in 3.5 to obtain the desired compounds (12) and (9).

3.10 Compounds (12) and (9) by cleaving —Z from (16) and (10)

The cleavage of compounds (16) and (10) to obtain (12) and (9) is carried out by the methods described in paragraph 3.2.

3.11 2,5-Bis-(dialkylamino)-tetralines (11) by reduction of amide precursors (10)

In the compounds of type (10), —Z has the meaning of an acid ester —$COR^7$ which can be converted, during the reduction step, analogously to the methods specified in Section 3.5, into a substituent —$R^3$ or —$R^4$ as defined for formula (1).

3.12 5-Alkylamino-2-dialkylamino-tetralines (9) by dealkylation of 5-dialkylamino analogs (11)

Dealkylations of compounds (11) to obtain compounds (9) can be carried out using methods as described in Section 3.4.

3.13 Enantiomerically pure compounds (1)

Enantiomerically pure compounds (1) ((−)-1) and (+)-(1)) can be prepared from the racemic compounds, for example, using known methods of racemate resolution. It is also possible to obtain enantiomerically pure compounds of general formula 1 starting from enantiomerically pure intermediate products. Finally, it is possible to prepare enantiomerically pure compounds of general formula 1 by stereoselective methods of synthesis.

3.14 Galenic preparations

The 2,5-diamino-tetraline derivatives of general formula I and the pharmacologically harmless acid addition salts thereof may be converted in known manner into the usual formulations such as tablets, coated tablets, pills, granules, aerosols, syrups, emulsions, suspensions and solutions using inert pharmaceutically acceptable carriers or solvents. The proportion of the pharmaceutically active compounds may be in the range from 0.5 to 90% by weight of the total composition, i.e. in quantities which are sufficient in order to achieve the dosage range specified hereinafter.

The formulations are prepared for example by extending the active substances with solvents and/or carriers, optionally using emulsifiers and/or dispersing agents, whilst if water is used as a diluent, for example, organic solvents may be used as solubilising agents or as auxiliary solvents.

Examples of excipients include water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as natural mineral powders (e.g. kaolins, clays, talc, chalk), synthetic mineral powders (e.g. highly dispersed silica and silicates), sugars (e.g. glucose, lactose and dextrose), emulsifiers (e.g. lignin, sulphite waste liquors, methyl cellulose, starch and polyvinylpyrrolidone) and lubricants (e.g. magnesium stearate, talc, stearic acid and sodium laurylsulphate).

The compositions are administered in the usual way, preferably by oral or parenteral route, more particularly through the tongue or intravenously. If they are taken orally, the tablets may of course contain in addition to the above-mentioned carriers, other additives such as sodium citrate, calcium carbonate and dicalcium phosphate together with various additives such as starch, preferably potato starch, gelatin and the like. It is also possible to add lubricants such as magnesium stearate, sodium laurylsulphate and talc in order to form tablets. In the case of aqueous suspensions, the active substances may be combined with various flavour enhancers or dyes in addition to the above-mentioned excipients.

The tablets may also consist of several layers. In the same way, coated tablets may be produced by coating cores which have been made analogously to the tablets with substances normally used for tablet coatings, e.g. collidone or shellac, gum arabic, talc, titanium dioxide or sugar. In order to achieve delayed release or prevent intolerance, the core may also consist of several layers. Similarly, the tablet coating may be made up of several layers in order to achieve delayed release and for this purpose the excipients given for the tablets may be used.

Elixirs of the active substances or combinations of active substances according to the invention may additionally contain a sweetener such as saccharin, cyclamate, glycerol or sugar as well as a flavour enhancer, e.g. a flavouring such as vanillin or orange extract. They may also contain suspension adjuvants or thickeners such as sodium carboxymethyl cellulose, wetting agents, such as condensation products of fatty alcohols with ethylene oxide or preservatives such as p-hydroxybenzoates. Injectable solutions are obtained in the usual way, e.g. by adding preservatives such as p-hydroxybenzoates or stabilisers such as complexones and bottling the solution in injection vials or ampoules.

Capsules containing the active substances or combinations of active substances may be produced, for example, by mixing the active substances with inert carriers such as lactose or sorbitol and enclosing them in gelatine capsules.

Suitable suppositories may be produced for example by mixing the active substances or combinations of active substances envisaged for this purpose with the usual carriers such as neutral fats or polyethyleneglycol or derivatives thereof.

For parenteral administration, solutions of the active substances may be used, with suitable liquid carrier materials.

The dosage for oral use is 1 to 300 mg, preferably between 5 and 150 mg.

However, it may possibly be necessary to deviate from these amounts depending on the body weight and method of administration, the individual reaction to the drug, the nature of the formulation and the time or period of time over which the drug is administered. Thus, in certain cases it may be possible to use less than the minimum quantity specified whereas in other cases the upper limit will have to be exceeded. If larger quantities are administered it may be advisable to divide them into several smaller doses over the day. Moreover, the compounds of general formula 1 and the acid addition salts thereof may also be combined with active substances of other kinds.

FORMULATION EXAMPLES

| 1. Tablets | |
|---|---|
| Compound according to Example 4.2.27 | 10.0 mg |
| Corn starch | 99.0 mg |
| Anhyd. calcium phosphate | 140.0 mg |
| Magnesium stearate | 1.0 mg |
| | 250.0 mg |

The ingredients are processed in the usual way to form tablets weighing 250 mg.

| 2. Capsules | |
|---|---|
| Compound according to Example 4.2.27 | 150.0 mg |
| Corn starch | 150.0 mg |
| | 300.0 mg |

The finely powdered ingredients are thoroughly mixed. 300 mg batches of the mixture are transferred into normal gelatine capsules.

The following Examples of preparation illustrate the invention without restricting it.

The Preparation Examples described hereinafter in paragraphs 4.1 to 4.10 correspond to the methods of preparation described above in sections 3.1 to 3.10 and illustrate the invention without restricting it.

4. EXAMPLES

4.1 Compounds (3) and (4) from (2)

Example 4.1.1

5-Acetylamino-2-n-propylamino-tetraline base, hydrobromide, methanesulphonate and hydrochloride 40.6 g (0.20 mol) of 5-acetylamino-2-tetralone, 35.5 g (0.60 mol) of n-propylamine, 31 g of molecular sieve (0.4 nm, 10 mesh ASTM) and 580 ml of ethanol are stirred together in a nitrogen atmosphere whilst 36.0 g (0.60 mol) of glacial acetic acid are added. The temperature is maintained at 30° to 35° C. by cooling. After all the glacial acetic acid has been added the mixture is stirred for a further 3 hours at ambient temperature. Then the molecular sieve is removed by suction filtering and washed with a little ethanol. The filtrate is hydrogenated at 20° C. under 2 bar of hydrogen in the presence of 2.5 g of platinum oxide. The uptake of hydrogen is complete when the calculated quantity has been consumed. The catalyst is suction filtered, washed with ethanol and the filtrate is concentrated by evaporation in a rotary evaporator, finally at 80° C. under a complete water-jet vacuum.

Base: 100 mg of the crude product are dissolved in 0.3 ml of acetone and the solution is mixed with 1.0 ml of petroleum ether. The pure base crystallises out and after standing overnight it is suction filtered, washed with a little solvent mixture and dried at 50° C. Yield 77 mg (77%), melting point 90° C.

Hydrobromide: 100 mg (0.41 mmol) of the crude base are dissolved in 1 ml of ethanol with the calculated quantity (0.17 ml) of 2.5 N ethanolic hydrobromic acid. After the addition of diethylether until turbidity is just beginning, crystallisation sets in. After standing for a period of about 12 hours at ambient temperature the mixture is suction filtered, washed with ethanol/ether and dried at 40° C. Yield 120 mg (92.3% of theory), melting point 271° C.

Methanesulphonate: 100 mg (0.41 mmol) of the crude base are dissolved in 1 ml of ethanol with the calculated quantity (0.17 ml) of 2.5 N ethanolic methanesulphonic acid. After diethylether has been added dropwise until turbidity is just beginning, crystallisation occurs. After standing for a period of about 12 hours at ambient temperature the mixture is suction filtered, washed with ethanol/ether and dried at 80° C. Yield 130 mg (94.9% of theory), melting point 167° C.

Hydrochloride: The remainder of the crude base is dissolved with 200 ml of ethanol and the solution is mixed with the quantity of 37% hydrochloric acid (19.7 g) calculated on the basis of the 5-acetyl-2-tetralone used (0.2 mol). The hydrochloride crystallises out of the solution, to which 400 ml of diethylether are added gradually with stirring. To complete crystallisation, the mixture is stirred for 2 hours in an ice bath, then suction filtered and washed with ethanol/ether 1:2. After drying, first in the air at ambient temperature and then in a drying chamber at 80° C. until a constant weight is obtained, 52.3 g of crystals are obtained with a melting point of 284° C., corresponding to a yield of 92.4% of theory. A sample recrystallised from methanol/ether melts unchanged at 284° C.

Example 4.1.2

5-Acetylamino-2-n-butylamino-tetraline-hydrochloride

Starting from 2.03 g (0.01 mol) of 5-acetylamino-2-tetralone and 2.2 g (0.03 mol) of n-butylamine, the title compound is obtained analogously to Example 4.1.1 in a yield of 2.0 g (67.4% of theory) and with a melting point of 281° C. which does not change after recrystallisation from methanol/ether.

Example 4.1.3

5-Acetylamino-2-sec-butylamino-tetraline-hydrochloride

Starting from 4.06 g (0.02 mol) of 5-acetylamino-2-tetralone and 4.4 g (0.06 mol) of sec.-butylamine the title compound is obtained analogously to Example 4.1.1 in a yield of 2.9 g (48.9% of theory) and with a melting point of 228° C. which does not change after recrystallisation from methanol/ether.

Example 4.1.4

5-Acetylamino-2-(2-phenylethyl-amino)-tetraline hydrochloride and base

Starting from 4.06 g (0.02 mol) of 5-acetylamino-2-tetralone and 7.3 g (0.06 mol) of 2-phenylethylamine, the hydrochloride of the title compound is obtained analogously to Example 4.1.1 in a yield of 4.8 g (69.7% of theory) and with a melting point of 288° C. which does not change after recrystallisation from methanol/water/ether.

For conversion into the base, 2.8 g (0.0081 mol) of the hydrochloride are shaken with 28 ml of water, 56 ml of methylene chloride and 2 ml of conc. ammonia. After separation of the phases, the aqueous layer is extracted twice more with 14 ml of methylene chloride. The combined methylene chloride extracts are washed with 20 ml of water, dried with sodium sulphate and evaporated down in a rotary evaporator, lastly at 80° C. under a complete water-jet vacuum, until a constant weight is achieved. The residue 2.5 g which crystallises spontaneously corresponds to a yield of 100%. M.p. 132°–134° C.

Example 4.1.5

5-Acetylamino-2-(3-phenylpropyl-amino)-tetraline hydrochloride and base

Starting from 4.06 g (0.02 mol) of 5-acetylamino-2-tetralone and 8.1 g (0.06 mol) of 3-phenylpropylamine, the hydrochloride of the title compound is obtained analogously to Example 4.1.1 in a yield of 5.4 g (75.2% of theory) and with a melting point of 270° C., which increases to 274° C. after recrystallisation from methanol/water/ether.

From 2.9 g of the hydrochloride (0.0081 mol) the base is obtained analogously to Example 4.1.4 in a yield of 100% and with a melting point of 75° to 76° C.

Example 4.1.6

5-Acetylamino-2-(4-phenylbutyl-amino)-tetralinehydrochloride

Starting from 3.4 g (0.0167 mol) of 5-acetylamino-2-tetralone and 7.5 g (0.05 mol) of 4-phenylbutylamine, the title compound is obtained analogously to Example 4.1.1 in a yield of 4.94 g (79.3% of theory) and with a melting point of 278° C., which does not change after recrystallisation from ethanol/ether.

Example 4.1.7

5-Acetylamino-2-(5-phenylpentyl-amino)-tetralinehydrochloride

Starting from 2.03 g (0.01 mol) of 5-acetamino-2-tetralone and 4.9 g (0.03 mol) of 5-phenylpentylamine, the title compound is obtained analogously to Example 4.1.1 in a yield of 3.25 g (84.0% of theory) and with a melting point of 270° C., which does not change after recrystallisation from methanol/ether.

Example 4.1.8

5-Acetylamino-2-(6-phenylhexyl-amino)-tetralinehydrochloride

Starting from 2.03 g (0.01 mol) of 5-acetylamino-2-tetralone and 5.3 g (0.03 mol) of 6-phenylhexylamine, the title compound is obtained analogously to Example 4.1.1 in a yield of 3.5 g (87.3% of theory) and with a melting point of 268° C., which does not change after recrystallisation from methanol/ether.

Example 4.1.9

5-Acetylamino-2-(9-phenylnonyl-amino)-tetralinehydrochloride

Starting from 3.07 g (0.015 mol) of 5-acetylamino-2-tetralone and 9.87 g (0.045 mol) of 9-phenylnonylamine, the title compound is obtained analogously to Example 4.1.1 in a yield of 5.35 g (80.5% of theory) and with a melting point of 272° C., which rises to 273° C. after recrystallisation from methanol/ether.

Example 4.1.10

5-Acetylamino-2-[2-(3-indolyl)-ethyl-amino]-tetraline base and hydrochloride

Starting from 6.1 g (0.03 mol) of 5-acetylamino-2-tetraline and 5.3 g (0.033 mol) of tryptamine (3-(2-aminoethyl)-indole), the title compound is obtained analogously to Example 4.1.1 in the form of the base. It is purified by column chromatography on silica gel (150 g) using a mixture of methylene chloride/methanol/conc. ammonia 90:10:0.5 as eluant. Yield 4.7 g (45.1% of theory).

To convert it into the hydrochloride 0.50 g of the base are dissolved in 5 ml of methanol with the calculated quantity of 2.5 N ethanolic hydrochloric acid. The solution is mixed with diethylether until turbidity is just beginning. The hydrochloride crystallises out and is obtained in a yield of 0.5 g (89.9% of theory) and melts at 256° C. After recrystallisation from ethanol the melting point does not change.

Example 4.1.11

5-Acetylamino-2-[2-(2-thienyl)-ethyl-amino]-tetralinehydrochloride 2.03 g of (0.01 mol) of 5-acetylamino-2-tetralone, 3.2 g (0.02 mol) of 2-(2-thienyl)-ethyl-aminehydrochloride and 0.75 g (0.012 mol) of sodium cyanoborohydride are dissolved in 30 ml of methanol and stirred for 24 hours at ambient temperature. The mixture is then acidified by the dropwise addition of conc. hydrochloric acid with stirring and cooling with ice. After 10 minutes, 100 ml of water is added whilst stirring continues and then a total of 4.0 g of anhydrous soda is added in batches. Then extraction is carried out with 50 ml of methylene chloride and twice with 25 ml of methylene chloride. The combined extracts are washed with 20 ml of water, dried with sodium sulphate and after separation of the drying agent, concentrated by evaporation in a rotary evaporator, finally at 90° C. and under a complete water-jet vacuum. The residue is dissolved with 5 ml of methanol and 4.0 ml of 2.5 N ethanolic hydrochloric acid and the solution is mixed with diethylether until turbidity is just beginning. After standing for a period of about 12 hours at 5° C. the title compound is suction filtered, washed with ethanol/ether and dried at 80° C. until the weight remains constant. Yield: 3.1 g (88.3% of theory), melting point 276° C. (unchanged after recrystallisation from methanol/ether).

Example 4.1.12

5-Acetylamino-2-ethylamino-tetraline-hydrochloride

Starting from 2.03 g (0.01 mol) of 5-acetylamino-2-tetralone and 2.45 g (0.03 mol) of ethylaminehydrochloride the title compound is obtained analogously to Example 4.1.11 in a yield of 1.2 g (44.6% of theory) and with a melting point of 351° C. which does not change after recrystallisation from methanol/ether.

Example 4.1.13

5-Acetylamino-2-allylamino-tetraline-hydrochloride

Starting from 3.04 g (0.015 mol) of 5-acetylamino-2-tetralone and 4.2 g (0.045 mol) of allylaminehydrochloride the title compound is obtained analogously to Example 4.1.11 in a yield of 3.30 g (78.4% of theory) and with a melting point of 263° C. which does not change after recrystallisation from methanol/water/ether.

Example 4.1.14

5-Acetylamino-2-propargylamino-tetraline-hydrochloride

Starting from 2.03 g (0.01 mol) of 5-acetylamino-2-tetralone and 1.37 g (0.015 mol) of propargylaminehyddrochloride the title compound is obtained analogously to Example 4.1.11 in a yield of 2.24 g (80.3% of theory) and with a melting point of 225° C., which does not change after recrystallisation from methanol/ether.

Example 4.1.15

5-Acetylamine-2-cyclopropylmethylamino-tetralinehydrochloride

Starting from 2.03 g (0.01 mol) of 5-acetylamino-2-tetralone and 1.61 g (0.015 mol) of cyclopropylmethylamine-hydrochloride the title compound is obtained analogously to Example 4.1.11 in a yield of 1.62 g (55.9% of theory) and with a melting point of 266° C., which does not change after recrystallisation from methanol/ether.

Example 4.1.16

5-Acetylamino-2-benzylamino-tetraline-hydrochloride

Starting from 4.06 g (0.02 mol) of 5-acetylamino-2-tetralone and 8.6 g (0.06 mol) of benzylaminohydrochloride the title compound is obtained analogously to Example 4.1.11 in a yield of 5.6 g (84.5% of theory) and with a melting point of 281° C., which does not change after recrystallisation from methanol/ether.

Example 4.1.17

5-Acetylamino-2-[2-(2-furyl)-ethyl-amino]-tetralinehydrochloride

Starting from 0.61 g (0.0031 mol) of 5-acetylamino-2-tetralone and 0.9 g (0.006 mol) of 2 (2-furyl)ethylamine-hydrochloride the title compound is obtained analogously to Example 4.1.11 in a yield of 0.8 g (77.1% of theory) and with a melting point of 256° C., which increases to 257° C. after recrystallisation from methanol/ether.

Example 4.1.18

5-Acetylamino-2-(cis-cinnamylamino)-tetralinehydrochloride

Starting from 1.02 g (0.005 mol) of 5-acetylamino-2-tetralone and 1.7 g (0.01 mol) of cis-cinnamyl-aminehydrochloride the title compound is obtained analogously to Example 4.1.11 in a yield of 1.35 g (76.5% of theory) and with a melting point of 246° C., which does not change after recrystallisation from methanol/ether.

Example 4.1.19

5-Acetylamino-2-(trans-cinnamylamino)-tetralinehydrochloride

Starting from 1.02 g (0.005 mol) of 5-acetylamino-2-tetralone and 1.7 g (0.01 mol) of trans-cinnamylamine-hydrochloride the title compound is obtained analogously to Example 4.1.11 in a yield of 1.1 g (61.6% of theory) and with a melting point of 257° C., which does not change after recrystallisation from methanol/ether.

Example 4.1.20

5-Acetylamino-2-furfurylamino-tetraline-hydrochloride

Starting from 2.03 g (0.01 mol) of 5-acetylamino-2-tetralone and 4.0 g (0.03 mol) of furfurylaminehydrochloride the title compound is obtained analogously to Example 4.1.11 in a yield of 2.1 g (65.4% of theory) and with a melting point of 296° C., which does not change after recrystallisation from methanol/ether.

Example 4.1.21

5-Acetylamino-2-(2-p-tolyl-ethyl-amino)-tetralinehydrochloride

Starting from 0.61 g (0.003 mol) of 5-acetylamino-2-tetralone the title compound is obtained analogously to Example 4.1.11 in a yield of 0.68 g (63.0% of theory) and with a melting point of 286° C.

Example 4.1.22

5-Acetylamino-2-(2-p-methoxyphenyl-ethyl-amino)tetraline-hydrochloride

Starting from 1.02 g (0.005 mol) of 5-acetylamino-2-tetralone the title compound is obtained analogously to Example 4.1.11 in a yield of 1.25 g (66.7% of theory) and with a melting point of 279° C.

Example 4.1.23

5-Acetylamino-2-(2-p-fluorophenyl-ethyl-amino)tetraline-hydrochloride

Starting from 0.61 g (0.003 mol) of 5-acetylamino-2-tetralone the title compound is obtained analogously to Example 4.1.11 in a yield of 0.65 g (60.0% of theory) and with a melting point of 280° C.

Example 4.1.24

5-Acetylamino-2-(2-m-methoxyphenyl-ethyl-amino)tetraline-hydrochloride

Starting from 1.02 g (0.005 mol) of 5-acetylamino-2-tetralone the title compound is obtained analogously to Example 4.1.11 in a yield of 1.25 g (66.7% of theory) and with a melting point of 269° C.

Example 4.1.25

5-Acetylamino-2-dimethylamino-tetraline-hydrochloride

Starting from 2.03 g (0.01 mol) of 5-acetylamino-2-tetralone and 2.45 g (0.03 mol) of dimethylaminohydrochloride the title compound is obtained analogously to Example 4.1.11 in a yield of 1.35 g (50.2% of theory) and with a melting point of 199° C. which does not change after recrystallisation from methanol/ether.

Example 4.1.26

5-Acetylamino-2-(N-benzyl-N-methyl-amino)-tetralinehydrochloride

Starting from 2.03 g (0.01 mol) of 5-acetylamino-2-tetralone and 4.37 g (0.03 mol) of N-benzylmethylaminehydrochloride the title compound is obtained analogously to Example 4.1.11 in a yield of 2.0 g (58.1% of theory) and with a melting point of 243° C. which does not change after recrystallisation from methanol/ether.

4.2 Compounds (5) and (6) from (4) and (3), respectively

Example 4.2.1

5-Amino-2-n-propylamino-tetraline (dihydrochloride and dihydrobromide)

2.82 g (0.01 mol) of 5-acetylamino-2-n-propylaminotetraline-hydrochloride (Example 4.1.1) are refluxed in 140 ml of 6 N HCl for 2.5 hours. Then the mixture is concentrated by rotary evaporation, finally at 80° C. under a complete water-jet vacuum. The residue is dissolved with 20 ml of methanol and 20 ml of diethylether are added dropwise to the solution with stirring. The title compound crystallises out in the form of the dihydrochloride. After standing for about 12 hours at 0° C. the mixture is suction filtered, washed with methanol/ether 1:1 and dried first in the air at ambient temperature and then at 80° C. until the weight remains constant. Yield 2.7 g (97.5% of theory), melting point >300° C. Recrystallisation from 50 ml of methanol, 10 ml of water and 100 ml of ether (yield 2.4 g) does not affect the melting point.

Analogously, by cleaving 0.20 g (0.7 mmol) of the starting compound with 48% hydrobromic acid, the title compound is obtained as a dihydrobromide in a yield of 0.21 g (81.7% of theory) and with a melting point of >300° C.

Example 4.2.2

5-Amino-2-n-butylamino-tetraline-dihydrochloride

Starting from 0.60 g (0.002 mol) of 5-acetylamino-2-n-butylamino-tetraline-hydrochloride (Example 4.1.2) the title compound is obtained analogously to Example 4.2.1 in a yield of 0.57 g (97.8% of theory) and with a melting point of 290° C. which does not change after recrystallisation from methanol/water/ether.

Example 4.2.3

5-Amino-2-sec-butylamino-tetraline-dihydrochloride

Starting from 0.50 g (0.0017 mol) of 5-acetylamino-2-sec-butylamino-tetraline-hydrochloride (Example 4.1.3) the title compound is obtained analogously to Example 4.2.1 in a yield of 0.45 g (90.9% of theory) and with a melting point of >300° C. which does not change after recrystallisation from methanol/ether.

Example 4.2.4

5-Amino-2-(2-phenylethyl-amino)-tetralinedihydrochloride

Starting from 1.00 g (0.0029 mol) of 5-acetylamino-2-(2-phenylethyl-amino)-tetraline-hydrochloride (Example 4.1.4) the title compound is obtained analogously to Example 4.2.1 in a yield of 0.95 g (96.5% of theory) and with a melting point of 325° C. which does not change after recrystallisation from methanol/water/ether.

Example 4.2.5

5-Amino-2-(3-phenylpropyl-amino)-tetralinedihydrochloride

Starting from 1.00 g (0.0028 mol) of 5-acetylamino-2-(3-phenylpropyl-amino)-tetraline-hydrochloride (Example 4.1.5) the title compound is obtained analogously to Example 4.2.1 in a yield of 0.90 g (91.4% of theory) and with a melting point of 325° C. which does not change after recrystallisation from methanol/water/ether.

Example 4.2.6

5-Amino-2 (4-phenylbutyl-amino)-tetralinedihydrochloride

Starting from 1.00 g (0.0027 mol) of 5-acetylamino-2-(4-phenylbutylamino)-tetraline-hydrochloride (Example 4.1.6) the title compound is obtained analogously to Example 4.2.1 in a yield of 0.96 g (97.5% of theory) and with a melting point of >300° C. which does not change after recrystallisation from methanol/ether.

Example 4.2.7

5-Amino-2-(5-phenylpentyl-amino)-tetralinedihydrochloride

Starting from 0.50 g (0.0013 mol) of 5-acetylamino-2-(5-phenylpentylamino)-tetraline-hydrochloride (Example 4.1.7) the title compound is obtained analogously to Example 4.2.1 in a yield of 0.47 g (95.3% of theory) and with a melting point of >300° C. which does not change after recrystallisation from methanol/water/ether.

Example 4.2.8

5-Amino-2-(6-phenylhexyl-amino)-tetralinedihydrochloride

Starting from 0.50 g (0.0013 mol) of 5-acetylamino-2-(6-phenylhexylamino)-tetraline-hydrochloride (Example 4.1.8) the title compound is obtained analogously to Example 4.2.1 in a yield of 0.47 g (95.3% of theory) and with a melting point of >300° C. which does not change after recrystallisation from methanol/water/ether.

Example 4.2.9

5-Amino-2-(9-phenylnonyl-amino)-tetralinedihydrochloride

Starting from 1.0 g (2.26 mol) of 5-acetylamino-2-phenylnonylamino)-tetraline-hydrochloride (Example 4.1.9) the title compound is obtained analogously to Example 4.2.1 in a yield of 0.90 g (91.9% of theory) and with a melting point of >300° C. which does not change after recrystallisation from methanol/water/ether.

Example 4.2.10

5-Amino-2-[2-(3-indolyl)-ethyl-amino]-tetralinedihydrochloride

Starting from 0.7 g (0.002 mol) of 5-acetylamino-2-[3-indolyl)-ethyl-amino]-tetraline (Example 4.1.10) the title compound is obtained analogously to Example 4.2.1 in a yield of 0.6 g (79.4% of theory) and with a melting point of >300° C.

Example 4.2.11

5-Amino-2-[2-(2-thienyl)-ethyl-amino]-tetralinedihydrochloride

Starting from 0.70 g (0.0026 mol) of 5-acetylamino-2-[2-(2-thienyl)-ethyl-amino]-tetraline-hydrochloride (Example 4.1.11) the title compound is obtained analogously to Example 4.2.1 in a yield of 0.60 g (66.7% of theory) and with a melting point of >300° C. which does not change after recrystallisation from methanol/water/ether.

Example 4.2.12

5-Amino-2-ethylamino-tetraline-dihydrochloride

Starting from 1.44 g (0.0054 mol) of 5-acetylamino-2-ethylamino-tetraline-hydrochloride (Example 4.1.12) the title compound is obtained analogously to Example 4.2.1 in a yield of 1.3 g (91.6% of theory) and with a melting point of >300° C. which does not change after recrystallisation from methanol/ether.

Example 4.2.13

5-Amino-2-allylamino-tetraline-dihydrochloride

Starting from 0.8 g (0.0029 mol) of 5-acetylamino-2-allylamino-tetraline-hydrochloride (Example 4.1.13) the title compound is obtained analogously to Example 4.2.1 in a yield of 0.75 g (78.4% of theory) and with a melting point of >300° C. which does not change after recrystallisation from methanol/water/ether.

Example 4.2.14

5-Amino-2-propargylamino-tetraline-dihydrochloride

Starting from 1.24 g (0.0045 mol) of 5-acetylamino-2-propargylamino-tetraline-hydrochloride (Example 4.1.14) the title compound is obtained analogously to Example 4.2.1 in a yield of 1.12 g (91.8% of theory) and with a melting point of 260° C.

Example 4.2.15

5-Amino-2-cyclopropylmethylamino-tetralinedihydrochloride

Starting from 0.90 g (0.0031 mol) of 5-acetylamino-2-cyclopropylmethyl amino-tetraline-hydrochloride (Example 4.1.15) the title compound is obtained analogously to Example 4.2.1 in a yield of 0.70 g (85.3% of theory) and with a melting point of >300° C. which does not change after recrystallisation from methanol/water/ether.

Example 4.2.16

5-Amino-2-benzylamino-tetraline-dihydrochloride

Starting from 0.50 g (0.0071 mol) of 5-acetylamino-2-benzylamino-amino-tetraline-hydrochloride (Example 4.1.16) the title compound is obtained analogously to Example 4.2.1 in a yield of 0.46 g (81.7% of theory) and with a melting point of 350° C. which does not change after recrystallisation from methanol/ether.

Example 4.2.17

5-Amino-2-[2-(2-furyl)-ethyl-amino]-tetralinedihydrochloride

Starting from 0.35 g (0.0011 mol) of 5-acetylamino-2-[2-(2-furyl)-ethyl-amino]-tetraline-hydrochloride (Example 4.2.1) the title compound is obtained analogously to Example 4.2.1 in a yield of 0.21 g (61.1% of theory) and with a melting point of >300° C. which does not change after recrystallisation from methanol/ether.

Example 4.2.18

5-Amino-2-(cis-cinnamylamino)-tetraline-dihydrochloride

Starting from 0.30 g (0.85 mol) of 5-acetylamino-2-(cis-cinnamylamino)-tetraline-hydrochloride (Example 4.1.18 the title compound is obtained analogously to Example 4.2.1 in a yield of 0.25 g (84.8% of theory) and with a melting point of 297° C. which does not change after recrystallisation from methanol/ether.

Example 4.2.19

5-Amino-2-(trans-cinnamylamino)-tetralinedihydrochloride

Starting from 0.40 g (0.0011 mol) of 5-acetylamino(-trans-cinnamylamino)-tetraline-hydrochloride (Example 4.1.19 the title compound is obtained analogously to Example 4.2.1 in a yield of 0.35 g (88.8% of theory) and with a melting point of 308° C. which does not change after recrystallisation from methanol/water/ether.

Example 4.2.20

5-Amino-2-furfurylamino-tetraline-dihydrochloride

Starting from 1.50 g (0.0053 mol) of 5-acetylamino-2-furfuryl-amino-tetraline-hydrochloride (Example 4.1.20 the title compound is obtained analogously to Example 4.2.1 in a yield of 1.35 g (80.8% of theory) and with a melting point of >300° C.

Example 4.2.21

5-Amino-2-(2-tolyl-ethyl-amino)-tetralinedihydrochloride

Starting from 0.36 g (0.001 mol) of 5-acetylamino-2-(2-p-tolyl-ethyl-amino)-tetraline-hydrochloride (Example 4.1.21) the title compound is obtained analogously to Example 4.2.1 in a yield of 0.34 g (96.2% of theory) and with a melting point of >300° C.

Example 4.2.22

5-Amino-2-(2-p-methoxyphenyl-ethyl-amino)-tetralinedihydrochloride

Starting from 0.75 g (0.002 mol) of 5-acetylamino-2-(2-p-methoxyphenyl-ethyl-amino)-tetralinehydrochloride (Example 4.1.22) the title compound is obtained analogously to Example 4.2.1 in a yield of 0.67 g (90.7% of theory) and with a melting point of >300° C.

Example 4.2.23

5-Amino-2-(2-p-fluorophenyl-ethyl-amino)-tetralinedihydrochloride

Starting from 0.36 g (0.001 mol) of 5-acetylamino-2-(2-p-fluorophenyl-ethyl-amino)-tetraline-hydrochloride (Example 4.1.23) the title compound is obtained analogously to Example 4.2.1 in a yield of 0.32 g (89.5% of theory) and with a melting point of >300° C.

Example 4.2.24

5-Amino-2-(2-m-methoxyphenyl-ethyl-amino)-tetralinedihydrochloride

Starting from 0.75 g (0.002 mol) of 5-acetylamino-2-(2-m-methoxyphenyl-ethyl-amino)-tetralinehydrochloride (Example 4.1.24) the title compound is obtained analogously to Example 4.2.1 in a yield of 0.66 g (89.3% of theory) and with a melting point of >300° C.

Example 4.2.25

5-Amino-2-dimethylamino-tetraline-dihydrochloride

Starting from 0.65 g (0.0024 mol) of 5-acetylamino-2-dimethylamino-tetraline-hydrochloride (Example 4.1.25) the title compound is obtained analogously to Example 4.2.1 in a yield of 0.30 g (63.2% of theory) and

Example 4.2.26

5-Amino-2-di-n-propylamino-tetraline-dihydrochloride

Starting from 2.70 g (0.0083 mol) of 5-acetylamino-2-di-n-propylamino-tetraline-hydrochloride (Example 4.3.4) the title compound is obtained analogously to Example 4.2.1 in a yield of 2.7 g (100% of theory) and with a melting point of 295° C. which does not change after recrystallisation from methanol/ether.

Example 4.2.27

5-Amino-2-methylamino-tetraline-dihydrochloride

Starting from 1.14 g (0.0045 mol) of 5-acetylamino-2-methylamino-tetraline-hydrochloride (Example 4.4.1) the title compound is obtained analogously to Example 4.2.1 in a yield of 1.05 g (93.8% of theory) and with a melting point of >300° C. which does not change after recrystallisation from methanol/ether.

Example 4.2.28

5-Amino-2-diethylamino-tetraline-dihydrochloride

Starting from 0.50 g (0.0017 mol) of 5-acetylamino-2-diethylamino-tetraline-hydrochloride (Example 4.3.3) the title compound is obtained analogously to Example 4.2.1 in a yield of 0.44 g (88.9% of theory) and with a melting point of 277° C. which does not change after recrystallisation from methanol/ether.

Example 4.2.29

5-Amino-2-(N-methyl-N-n-propyl-amino)-tetralinedihydrochloride

Starting from 1.10 g (0.0037 mol) of 5-acetylamino-2-(N-methyl-N-n-propyl-amino)-tetraline-hydrochloride (Example 4.3.7) the title compound is obtained analogously to Example 4.2.1 in a yield of 0.62 g (57.4% of theory) and with a melting point of 284° C. which does not change after recrystallisation from methanol/water/ether.

Example 4.2.30

5-Amino-2-(N-ethyl-N-n-propyl-amino)-tetralinedihydrochloride

Starting from 1.00 g (0.0032 mol) of 5-acetylamino-2-(N-ethyl-N-n-propyl-amino)-tetraline-hydrochloride (Example 4.3.2) the title compound is obtained analogously to Example 4.2.1 in a yield of 0.90 g (92.9% of theory) and with a melting point of 284° C. which does not change after recrystallisation from methanol/ether.

Example 4.2.31

5-Amino-2-(N-n-butyl-N-n-propyl-amino)-tetralinedihydrochloride

Starting from 1.25 g (0.0037 mol) of 5-acetylamino-2-(N-n-butyl-N-n-propyl-amino)-tetraline-hydrochloride (Example 4.3.1) the title compound is obtained analogously to Example 4.2.1 in a yield of 1.10 g (89.4% of theory) and with a melting point of 270° C. which does not change after recrystallisation from methanol/ether.

Example 4.2.32

5-Amino-2-[N-n-propyl-N-2-(2-thienyl)-ethyl-amino]-tetraline

Starting from 2.20 g (0.0062 mol) of 5-acetylamino-2-[N-n-propyl-N-2-(2-thienyl)-ethyl-amino]-tetraline the title compound is obtained analogously to Example 4.2.1 in the form of the hydrochloride, which could not be crystallised. The base purified by column chromatography analogously to Example 4.1.10 could not be crystallised either. Yield of amorphous substance 1.4 g (72.2% of theory).

Example 4.2.33

5-Amino-2-(7-phenylheptyl-amino)-tetralinedihydrochloride

Starting from 0.60 g (1.45 mol) of 5-acetylamino-2-(7-phenylheptyl-amino)-tetraline-hydrochloride (Example 4.4.2) the title compound is obtained analogously to Example 4.2.1 in a yield of 0.58 g (97.6% of theory) and with a melting point of >300° C. which does not change after recrystallisation from methanol/water/ether.

Example 4.2.34

5-Amino-2-(8-phenyloctyl-amino)-tetralinedihydrochloride

Starting from 0.50 g (1.16 mol) of 5-acetylamino-2-(8-phenyloctyl-amino)-tetraline-hydrochloride (Example 4.4.3) the title compound is obtained analogously to Example 4.2.1 in a yield of 0.45 g (91.3% of theory) and with a melting point of >300° C. which does not change after recrystallisation from methanol/water/ether.

4.3 Compounds (3) and (4) from (13) and (13), respectively

Example 4.3.1

5-Acetylamino-2-(N-n-butyl-N-n-propyl-amino)-tetralinehydrochloride 2.83 g (0.010 mol) of 5-acetylamino-2-n-propylamino-tetraline-hydrochloride (Example 4.1.1), 2.76 g (0.015 mol) of n-butyliodide and 1.68 g (0.020 mol) of sodium hydrogen carbonate are refluxed in a mixture of 20 ml of absolute dimethylformamide and 30 ml of absolute tetrahydrofuran for 48 hours with stirring (moment of complete reaction determined by thin layer chromatography). The reaction mixture is concentrated by rotary evaporation, finally at 95° C. under a complete water-jet vacuum. The residue is shaken with 50 ml of methylene chloride and 50 ml of water and the aqueous phase separated is extracted twice more with 15 ml of methylene chloride. The combined extracts are washed with 20 ml of water, dried with sodium sulphate and concentrated by rotary evaporation, finally at 90° C. under a complete water-jet vacuum. The residue is dissolved with 10 ml of ethanol and the solution is acidified with 4.0 ml of 2.5 N ethanolic hydrochloric acid (0.0I mol HCl). After the addition of diethylether until turbidity is just starting, the title compound crystallises. After standing overnight it is suction filtered at 5° C., washed with a mixture of ethanol and ether and dried at 80° C. until a constant weight is obtained. Yield 2.56 g (75.5% of theory), melting point 217° C. After recrystallisation from methanol/ether the melting point does not change.

Example 4.3.2

5-Acetylamino-2-(N-ethyl-N-n-propyl-amino)-tetralinehydrochloride

Starting from 2.83 g (0.01 mol) of 5-acetylamino-2-n-propylamino-tetraline-hydrochloride (Example 4.1.1)

the title compound is obtained analogously to Example 4.3.1 in a yield of 2.09 g (67.2% of theory) and with a melting point of 206° C. which rises to 209° C. after recrystallisation from methanol/ether.

Example 4.3.3

5-Acetylamino-2-diethylamino-tetraline-hydrochloride

Starting from 2.00 g (0.0074 mol) of 5-acetylamino-2-ethylamino-tetraline (Example 4.1.12) the title compound is obtained, analogously to Example 4.3.1, using 2.8 g (0.018 mol) of ethyliodide and a reaction time of 32 hours, in a yield of 0.90 g (43.2% of theory) and with a melting point of 225° C., which does not change after recrystallisation from methanol/ether.

Example 4.3.4

5-Acetylamino-2-di-n-propylamino-tetraline

Starting from 2.46 g (0.010 mol) of 5-acetylamino-2-n-propylamino-tetraline (Example 4.1.1) the title compound is obtained analogously to Example 4.3.1 as the evaporation residue of the methylene chloride extracts, which crystallises out (2.7 g, 93.6% of theory). A sample recrystallised from acetone melts at 101° C.

Example 4.3.5

5-Acetylamino-2-[(N-benzyl-N-(7-phenylheptyl)-amino]-tetraline

Starting from 3.31 g (0.010 mol) of 5-acetylamino-2-benzylamino-tetraline-hydrochloride (Example 4.1.16) the title compound is obtained analogously to Example 4.3.1 using 5.62 g (0.022 mol) of 7-phenyl-heptylbromide and after a reaction time of 60 hours and the title compound is subjected to catalytic debenzylation without any further purification (cf. Example 4.4.2).

Example 4.3.6

5-Acetylamino-2-[N-benzyl-N-(8-phenyloctyl)-amino]-tetraline

Starting from 3.31 g (0.010 mol) of 5-acetylamino-2-benzylamino-tetraline-hydrochloride (Example 4.1.16) the title compound is obtained analogously to Example 4.3.1 using 5.92 g (0.022 mol) of 8-phenyl-octylbromide after a reaction time of 55 hours and is subjected to catalytic debenzylation without further purification (cf. Example 4.4.3).

Example 4.3.7

5-Acetylamino-2-(N-methyl-N-n-propyl-amino)-tetraline 2.46 g (0.010 mol) of 5-acetylamino-2-n-propylamino-tetraline (Example 4.1.1) are heated with 2.34 g (0.050 mol) of formic acid and 2.2 ml of 30% formalin solution (0.022 mol of formaldehyde) for 30 minutes over a boiling water bath. The reaction mixture is shaken with 50 ml of water, 50 ml of methylene chloride and 2 ml of conc. ammonia. The aqueous phase separated off is extracted twice more with 15 ml of methylene chloride. The combined methylene chloride extract are washed with 20 ml of water, dried with sodium sulphate and concentrated by evaporation, after removal of the drying agent, in a rotary evaporator, finally at 80° C. under a total water jet vacuum. The residue is crystallised from 5 ml of acetone and 20 ml of petroleum ether. The title compound is obtained in a yield of 1.80 g (69.2% of theory) and with a melting point of 78° C.

Example 4.3.8

5-Acetylamino-2-methylamino-tetraline-hydrochloride

Starting from 0.28 g (0.0014 mol) of 5-acetylamino-2-amino-tetraline, 0.33 g (0.007 mol) of formic acid and 0.07 g of 30% formalin solution (0.7 mmol $CH_2O$) the 5-acetylamino-2-methylamino-tetraline is obtained analogously to Example 4.3.7 together with its 2-dimethylamino-homologues and unreacted starting material. The title compound is separated by column chromatography on silica gel with methylene chloride/methanol/conc. ammonia 80:20:1 and crystallised as the hydrochloride. Yield 0.1 g (30.8% of theory), melting point 253° C.

4.4 Compounds (3) from (4)

Example 4.4.1

5-Acetylamino-2-methylamino-tetraline-hydrochloride 1.40 g (0.0041 mol) of 5-acetylamino-2-(N-benzyl-N-methylamino)-tetraline-hydrochloride (Example 4.1.26) are hydrogenated in 50 ml of methanol in the presence of 0.4 g of 10% palladium/charcoal at 60° C. under a pressure of 4 bar until the uptake of hydrogen has ceased. After the catalyst has been removed by suction filtering, the residue is concentrated by rotary evaporation, finally at 80° C. under a complete water-jet vacuum. The residue is crystallised from 15 ml of methanol and 15 ml of diethylether. After suction filtering, washing with methanol/ether and drying at 80° C. the title compound is obtained in a yield of 0.85 g (81.5% of theory) and with a melting point of 253° C., which does not change after recrystallisation from methanol/ether.

Example 4.4.2

5-Acetylamino-2-(7-phenylheptyl-amino)-tetralinehydrochloride

Starting from the 5-acetylamino-2-[N-benzyl-N-(7-phenylheptyl) amino]-tetraline prepared according to Example 4.3.5 the title compound is obtained analogously to Example 4.4.1 in the form of the base, which is converted into the hydrochloride analogously to Example 4.1.1. Yield 3.10 g (74.7% of theory) over both stages of synthesis, melting point 260° C., unchanged after recrystallisation from methanol/ether.

Example 4.4.3

5-Acetylamino-2-(8-phenyloctyl-amino)-tetralinehydrochloride

Starting from the 5-acetylamino-2-[N-benzyl-N-(8-phenyloctyl)-amino]-tetraline prepared according to Example 4.3.6 the title compound is obtained analogously to Example 4.4.3 in a yield of 2.05 g (47.8% of theory over both stages of synthesis) and with a melting point of 259° C. which does not change after recrystallisation from methanol/ether.

4.5 Compounds (5) and (6) from (8) and (15) via intermediate products (7) and (14), respectively

Example 4.5.1

5-Amino-2-di-n-propylamino-tetraline-dihydrochloride (a)
4-Acetylamino-2-(n-propionyl-N-n-propyl-amino)tetraline 32.0 g (0.10 mol) of 5-acetylamino-2-n-propylamino-tetraline-hydrochloride (Example 4.1.1) and 25.3 g (0.25 mol) of triethylamine are vigorously stirred in 500 ml of absolute methylene chloride for 1 hour. Then 10.2 g (0.11 mol) of propionyl chloride dissolved in 50 ml of absolute methylene chloride are added dropwise within 30 minutes, with further stirring and reflux cooling. The reaction mixture is then refluxed for 1.5 hours. After cooling it is washed three times with 100 ml of water, dried with sodium sulphate and after separation of the drying agent concentrated by rotary evaporation, finally under a complete water-jet vacuum at a bath temperature of 80° C.

(b)
5-Amino-2-(N-propionyl-N-n-propyl-amino)-tetraline

The evaporation residue from reaction step a) is dissolved in a mixture of 250 ml of ethanol and 250 ml of 6 N hydrochloric acid and the solution is refluxed for 2.5 hours. After the majority of the ethanol has been distilled off in a rotary evaporator the mixture is cooled, combined with 250 ml of methylene chloride and made ammoniacal whilst cooling with ice (100 ml of conc. ammonia). The methylene chloride phase is separated off and the aqueous phase is extracted twice more with 100 ml of methylene chloride. The combined methylene chloride extracts are washed with 50 ml of water, dried with sodium sulphate and concentrated by rotary evaporation, after removal of the drying agent, finally at 80° C. and under a complete water-jet vacuum until a constant weight is obtained. Residue 25.5 g.

(c)
5-Amino-2-di-n-propylamino-tetraline-dihydrochloride

The evaporation residue from step b) is dissolved in 400 ml of absolute tetrahydrofuran. The solution is added dropwise, with stirring and cooling with ice, at 5° to 10° C., to a suspension of 11.4 g (0.30 mol) of lithium aluminium hydride in 300 ml of absolute tetrahydrofuran within a period of about 45 minutes and the reaction mixture is then refluxed for 1 hour with stirring. After cooling, 130 ml of water are added dropwise with vigorous stirring and cooling with ice. After the subsequent addition of 1300 ml of saturated diammonium tartrate solution the mixture is shaken thoroughly and separated in a separating funnel. The tetrahydrofuran phase is concentrated by rotary evaporation and the aqueous phase is extracted first with 250 ml and then with 100 ml of methylene chloride. The evaporation residue is dissolved with the combined methylene chloride extracts and, after washing with 50 ml of water, drying with sodium sulphate and removal of the drying agent by filtering, the solution is evaporated down (rotary evaporator, finally at 80° C. with a complete water-jet vacuum). The residue (24 g) is dissolved with 20 ml of methanol and 90 ml of 2.5 N ethanolic hydrochloric acid and the solution is mixed with 100 ml of diethylether. The title compound crystallises out and after being left to stand for about 12 hours at 5° C. it is suction filtered and washed with methanol/ether, then dried first in the air at ambient temperature and subsequently in a drying chamber at 80° C. until the weight remains constant. The title compound is obtained over three reaction steps with a total yield of 28.7 g (89.9% of theory) with a melting point of >300° C., which remains unchanged after recrystallisation from methanol/ether.

Example 4.5.2

5-Amino-2-[N-(2-phenylethyl)-N-propyl-amino]-tetralinedihydrochloride

Starting from 2.82 g (0.0091 mol) of 5-acetylamino-2-(2-phenylethylamino)-tetraline (Example 4.1.4) the title compound is obtained analogously to Example 4.5.1 by means of the intermediate products 5-acetylamino-2[N-propionyl-N-(2-phenyl-ethyl)-amino]-tetraline (3.3 g=90.5% of theory, melting point 143°-145° C.) and 5-amino-2-[N-propionyl-2-(2-phenylethyl)-amino]-tetraline (2.2 g=75.0% of theory, melting point 165°-166° C.) in a total yield of 2.30 g (66.3%) and with a melting point of 248°-250° C. (after sintering at 187°-190° C.), which does not change after recrystallisation from methanol/water/ether.

Example 4.5.3

5-Amino-2-[N-(3-phenylpropyl)-N-n-propyl-amino]-tetraline-dihydrochloride

Starting from 2.80 g (0.0081 mol) of 5-acetylamino-2-(3-phenylpropyl-amino)-tetraline (Example 4.1.5) the title compound is obtained analogously to Example 4.5.1 via the intermediate products 5-acetylamino-2-[N-propionyl-N-(3-phenylpropyl)-amino]-tetraline (3.5 g, melting point 148°-150° C.) and 5-amino-2-[N-propionyl-N(3-phenylpropyl)-amino]-tetraline (2.8 g) in a total yield of 2.91 g (90.5% of theory) and with a melting point of 135°-137° C.

Example 4.5.4

5-Amino-2-[N-(4-phenylbutyl N-n-propyl-amino]-tetralinedihydrochloride

Starting from 3.50 g (0.0094 mol) of 5-acetylamino-2-(4-phenylbutylamino)-tetraline-hydrochloride (Example 4.1.6) the title compound is obtained analogously to Example 4.5.1 via the intermediate products 5-acetylamino-2-[N-propionyl-N-(4-phenylbutyl)-amino]-tetraline and 5-amino-2-[N-propionyl-N-(4-phenylbutyl)amino]-tetraline in a total yield of 1.95 g (50.4% of theory) and with a melting point of 160° C. which does not change after recrystallisation from methanol/ether.

Example 4.5.5

5-Amino-2-[N-(5-phenylpentyl)-N-n-propyl-amino]-tetraline-dihydrochloride

Starting from 2.00 g (0.0052 mol) of 5-acetylamino-2-(5-phenylpentylamino)-tetraline-hydrochloride (Example 4.1.7) the title compound is obtained analogously to Example 4.5.1 via the intermediate products 5-acetylamino-2-[N-propionyl-N-(5-phenylpentyl)-amino]-tetraline and 5-amino-2-[N-propionyl-N-(5-phenylpentyl)amino]-tetraline in a total yield of 1.7 g (77.3% of theory) and with a melting point of 240° C. which does not change after recrystallisation from methanol/ether.

Example 4.5.6

5-Amino-2-[N-(6-phenylhexyl)-N-n-propylamino]-tetralinedihydrochloride

Starting from 2.20 g (0.0055 mol) of 5-acetylamino-2-(6-phenylhexylamino)-tetraline-hydrochloride (Example 4.1.8) the title compound is obtained analogously to Example 4.5.1 via the intermediate products 5-acetylamino-2-[N-propionyl-N-(6-phenylhexyl)-amino]-tetraline and 5-amino-2-[N-propionyl-N-(6- phenylhexyl)amino]-tetraline in a total yield of 1.9 g (79.2% of theory) and with a melting point of 242° C. which does not change after recrystallisation from methanol/ether.

Example 4.5.7

5-Amino-2-[N-(7-phenylheptyl)-N-n-propyl-amino]-tetraline dihydrochloride

Starting from 2.00 g (4.82 mol) of 5-acetylamino-2-(7-phenylheptyl-amino)-tetraline-hydrochloride (Example 4.4.2) the title compound is obtained analogously to Example 4.5.1 via the intermediate products 5-acetylamino-2-[N-propionyl-N-(7-phenylheptyl)-amino]-tetraline and 5-amino-2-[N-propionyl-N-(7-phenylheptyl)amino]-tetraline in a total yield of 1.32 g (60.7% of theory) and with a melting point of 231° C. which does not change after recrystallisation from methanol/ether.

Example 4.5.8

5-Amino-2-[N-(8-phenyloctyl)-N-n-propyl-amino]-tetraline dihydrochloride

Starting from 1.00 g (2.33 mol) of 5-acetylamino-2-(8-phenyloctyl-amino)-tetraline-hydrochloride (Example 4.4.3) the title compound is obtained analogously to Example 4.5.1 via the intermediate products 5-acetylamino-2-[N-propionyl-N-(8-phenyl-octyl)-amino]-tetraline and 5-amino-2-[N-propionyl-N-(8-phenyloctyl)amino]-tetraline in a total yield of 0.55 g (50.7% of theory) and with a melting point of 225° C. which does not change after recrystallisation from methanol/ether.

Example 4.5.9

5-Amino-2-[N-(9-phenylnonyl)-N-n-propyl-amino]-tetraline dihydrochloride

Starting from 3.20 g (0.0072 mol) of 5-acetylamino-2-(9-phenylnonyl-amino)-tetraline-hydrochloride (Example 4.1.9) the title compound is obtained analogously to Example 4.5.1 via the intermediate products 5-acetylamino-2-[N-propionyl-N-(9-phenylnonyl)-amino]-tetraline and 5-amino-2-[N-propionyl-N-(9-phenylnonyl)amino]-tetraline in a total yield of 2.4 g (69.3% of theory) and with a melting point of 228° C. which does not change after recrystallisation from methanol/ether.

Example 4.5.10

5-Amino-2-[N-(cis-cinnamyl)-N-n-propyl-amino]-tetralinedihydrochloride

Starting from 0.50 g (0.0014 mol) of 5-acetylamino-2-(cis-cinnamyl-amino)-tetraline-hydrochloride (Example 4.1.18) the title compound is obtained analogously to Example 4.5.1 via the intermediate products 5-acetylamino-2-[N-(cis-cinnamyl)-N-(propionyl-amino]-tetraline and 5-amino-[N-(cis-cinnamyl)-N-(propionylamino]-tetraline in a total yield of 0.22 g (41.9% of theory) and with a melting point of 166° C. which does not change after recrystallisation from methanol/ether.

Example 4.5.11

5-Amino-2-[N-(trans-cinnamyl)-N-n-propyl-amino]-tetraline-dihydrochloride

Starting from 1.00 g (0.0028 mol) of 5-acetylamino-2-(trans-cinnamyl-amino)-tetraline-hydrochloride (Example 4.1.19) the title compound is obtained analogously to Example 4.5.1 via the intermediate products 5-acetylamino-2-[N-(trans-cinnamyl)-N-propionyl-amino]-tetraline and 5-amino-2-[N-(trans-cinnamyl)-N-propionyl-amino]-tetraline in a total yield of 0.28 g (26.7% of theory) and with a melting point of 172° C. which does not change after recrystallisation from methanol/ether.

Example 4.5.12

2-[N-Allyl-N-n-propyl-amino]-5-amino-tetralinedihydrochloride

Starting from 1.80 g (0.0064 mol) of 5-acetylamino-2-(allylamino)-tetraline-hydrochloride (Example 4.1.13) the title compound is obtained analogously to Example 4.5.1 via the intermediate products 5-acetylamino-2-(N-allyl-N-propionyl-amino)-tetraline and 2-(N-allyl-N-propionyl-amino)-5-amino-tetraline in a total yield of 1.15 g (57.5% of theory) and with a melting point of 268° C. which does not change after recrystallisation from methanol/ether.

4.6 Compounds (12) and (9) from (3) and (4). respectively

Example 4.6.1

5-Ethylamino-2-n-propylamino-tetraline-dihydrochloride 1.00 g (0.0041 mol) of 5-acetylamino-2-n-propylamino-tetraline (Example 4.1.1) are dissolved in 10 ml of absolute tetrahydrofuran. The solution is added dropwise, with stirring and cooling with ice, to a suspension of 0.31 g (0.0081 mol) of lithium aluminium hydride in 10 ml of absolute tetrahydrofuran. The reaction mixture is then refluxed for 2 hours. It is then hydrolysed with 1.0 ml of water, with stirring and cooling with ice. After the addition of 30 ml of saturated diammonium tartrate solution the mixture is worked up analogously to Example 4.5.1, c). The title compound is obtained in the form of the base which is purified by column chromatography using 50 g of silica gel and methylene chloride/methanol/conc. ammonia 80:20:1 as eluant. The purified base is converted into the hydrochloride analogously to Example 4.1.1 using two equivalents of ethanolic hydrochloric acid and the hydrochloride is isolated in a yield of 0.18 g (14.4% of theory). Melting point 190° C., unchanged after recrystallisation from an ethanol/ether mixture.

Example 4.6.2

2-Di-n-propylamino-5-n-propylamino-tetralinedihydrochloride

Starting from 1.00 g (0.0033 mol) of 2-di-n-propylamino-5-propionyl-amino-tetraline (Example 4.7.3, base form) the title compound is obtained analogously to Example 4.6.1 in the form of the base purified by column chromatography. This is crystallised as the dihydrobromide analogously to Example 4.1.1 using two equivalents of ethanolic 2.5 N hydrobromic acid. Yield 0.35 g (23.5% of theory), melting point 203° C., unchanged after recrystallisation from ethanol/ether.

4.7 Compounds (10) and (16) from (4) and (3), respectively

Example 4.7.1

5-(N-Acetyl-N-methyl-amino)-2-di-n-propylamino-tetraline 0.38 g of a 75% suspension of sodium hydride in paraffin oil (0.012 mol) are added to a mixture of 40 ml of absolute dimethylformamide and 5 ml of absolute tetrahydrofuran. Then 2.88 g (0.010 mol) of 5-acetyl-2-di-n-propylamino-tetraline (Example 4.3.4) dissolved in 10 ml of absolute dimethylformamide are added with stirring and cooling with ice. Then the mixture is stirred at ambient temperature until the reaction is complete (several hours; monitored by DC). After concentration by rotary evaporation, finally at 95° C. under a complete water-jet vacuum, the residue is shaken with 50 ml of water and 50 ml of methylene chloride. The aqueous phase separated off is extracted twice more with 15 ml of methylene chloride. The combined extracts are washed with 20 ml of water, dried with sodium sulphate and, after the drying agent has been filtered off, concentrated by rotary evaporation, finally at 80° C. under a complete water-jet vacuum. The residue cannot be crystallised either as a base or as a salt. Therefore it is purified by column chromatography on 150 g of silica gel with methylene chloride/methanol/conc. ammonia 90:10:0.5. The substance purified in this way (2.8 g, 92.6% of theory) does not crystallise either, even though it is pure according to thin layer chromatography (silica gel, above-mentioned mixture of solvents, $R_f = 0.64$) and by NMR spectroscopy.

Example 4.7.2

5-(N-Acetyl-N-ethyl-amino)-2-di-n-propylamino-tetraline

Starting from 2.88 g (0.010 mol) of 5-acetylamino-2-n-dipropylamino-tetraline (Example 4.3.4) and 1.87 g (0.012 mol) of ethyliodide, the title compound is obtained analogously to Example 4.7.1 in the form of a non-crystallising gum in a yield of 2.65 g (83.7% of theory) and with an $R_f$ value of 0.65 (solvent mixture as specified in 4.7.1).

Example 4.7.3

5-(N-Acetyl N-n-propyl-amino)-2-di-n-propylaminotetraline

Starting from 2.88 g (0.010 mol) of 5-acetylamino-2-di-n-propylamino-tetraline (Example 4.3.4) and 2.04 g (0.012 mol) of n-propyliodide, the title compound is obtained analogously to Example 4.7.1 in the form of a non-crystallising gum in a yield of 2.70 g (89.4% of theory) and with an $R_f$ value of 0.67 (solvent mixture as specified in 4.7.1).

Example 4.7.4

5-(N-Acetyl-N-n-butyl-amino)-2-di-n-propylaminotetraline

Starting from 2.88 g (0.010 mol) of 5-acetylamino-2-di-n-propylamino-tetraline (Example 4.3.4) and 2.2 g (0.012 mol) of n-butyliodide, the title compound is obtained analogously to Example 4.7.1 in the form of a non-crystallising gum in a yield of 2.9 g (87.8% of theory) and with an $R_f$ value of 0.69 (solvent mixture as specified in 4.7.1).

Example 4.7.5

5-(N-Acetyl-N-allyl-amino)-2-di-n-propylamino-tetraline

Starting from 2.88 g (0.010 mol) of 5-acetylamino-2-di-n-propylamino-tetraline (Example 4.3.4) and 1.45 g (0.012 mol) of allylbromide, the title compound is obtained analogously to Example 4.7.1 in the form of a non-crystallising syrup in a yield of 2.25 g (68.4% of theory) and with an $R_f$ value of 0.66 (solvent mixture as specified in 4.7.1).

Example 4.7.6

5-(N-Acetyl-N-propargyl-amino)-2-di-n-propylaminotetraline

Starting from 2.88 g (0.010 mol) of 5-acetylamino-2-di-n-propylamino-tetraline (Example 4.3.4) and 1.43 g (0.012 mol) of propargylbromide the title compound is obtained analogously to Example 4.7.1 in the form of a non-crystallising, extremely viscous oil in a yield of 2.33 g (71.4% of theory) and with an $R_f$ value of 0.66 (solvent mixture as specified in 4.7.1).

Example 4.7.7

5-(N-Acetyl-N-benzyl-amino)-2-di-n-propylamino-tetraline

Starting from 2.55 g (0.010 mol) of 5-acetylamino-2-di-n-propylamino-tetraline (Example 4.3.4) and 1.50 g (0.012 mol) of benzyl chloride the title compound is obtained analogously to Example 4.7.1 in the form of a gum in a yield of 3.0 g (79.0% of theory).

Example 4.7.8

5-(N-Acetyl-N-methyl-amino)-2-n-propylamino-tetralinehydrochloride

Starting from 1.15 g (0.0047 mol) of 5-acetylamino-2-n-propylamino-tetraline (Example 4.1.1) and 0.54 g (0.0049 mol) of methyl methanesulphonate, the base of the title compound is obtained analogously to Example 4.7.1 and is crystallised as the hydrochloride after column chromatography. Yield 0.66 g (47.1% of theory), melting point 252°–253° C.

Example 4.7.9

5-(N-Acetyl-N-ethyl-amino)-2-n-propylamino-tetralinehydrochloride

Starting from 2.35 g (0.0095 mol) of 5-acetylamino-2-n-propylamino-tetraline (Example 4.1.1) and 1.07 g (0.0098 mol) of ethylbromide the base of the title compound is obtained analogously to Example 4.7.1 and crystallised as the hydrochloride. Yield 1.60 g (54.2% of theory), melting point 257° C.

Example 4.7.10

5-(N-Acetyl-N-allyl-amino)-2-n-propylamino-tetralinehydrochloride

Starting from 1.23 g (0.0050 mol) of 5-acetylamino-2-n-propylamino-tetraline (Example 4.1.1) and 0.64 g (0.0053 mol) of allylbromide the base of the title compound is obtained analogously to Example 4.7.1 and crystallised as the hydrochloride. Yield 0.82 g (49.4% of theory), melting point 237°–238° C.

Example 4.7.11

5-(N-Acetyl-N-propargyl-amino)-2-n-propylaminotetraline-hydrochloride

Starting from 1.23 g (0.005 mol) of 5-acetylamino-2-n-propylamino-tetraline (Example 4.1.1) and 0.63 g (0.0053 mol) of propargylbromide the base of the title compound is obtained analogously to Example 4.7.1 and crystallised as the hydrochloride. Yield 0.89 g (55.6% of theory), melting point 211° C.

Example 4.7.12

5-(N-Acetyl-N-cinnamyl-amino)-2-n-propylamino-tetralinehydrochloride

Starting from 1.23 g (0.005 mol) of 4-acetylamino-2-n-propylamino-tetraline (Example 4.1.1) and 0.85 g (0.0053 mol) of cinnamylbromide the base of the title compound is obtained analogously to Example 4.7.1 and crystallised as the hydrochloride. Yield 1.63 g (81.5% of theory), melting point 233° C.

4.8 Compounds (4) and (10) from (5) and (9)

Example 4.8.1

5-Acetylamino-2-[N-(4-phenylbutyl)-N-n-propyl-amino]-tetraline 0.90 g (0.0022 mol) of 5-amino-2-[N-(4-phenylbutyl)-N-n-propyl-amino]-tetraline-dihydrochloride (Example 4.5.4) and 1.00 g (0.0099 mol) of triethylamine are mixed with 15 ml of absolute methylene chloride with stirring and cooling with ice and 0.20 g (2.55 mmol) of acetylchloride in 5 ml of absolute methylene chloride are added. After 3 hours at ambient temperature or 30 minutes refluxing, the mixture is extracted three times with 5 ml of water, dried with sodium sulphate and concentrated by rotary evaporation, finally at 80° C. under a complete water-jet vacuum. The residue is crystallised from diethylether/petroleum ether.

Example 4.8.2

5-Acetylamino-2-[N-(5-phenylpentyl)-N-n-propyl-amino]-tetraline

Starting from 1.20 g (2.83 mmol) of 5-amino-2-[N-(5-phenylpentyl)-N-n-propyl-amino]-tetralinedihydrochloride (Example 4.5.5) the title compound is obtained analogously to Example 4.8.1 using acetic anhydride instead of acetyl chloride in a yield of 0.90 g (80.9% of theory) and with a melting point of 70° C. which does not change after recrystallisation from ether/petroleum ether.

Example 4.8.3

2-Di-n-propylamino-5-propionylamino-tetralinehydrochloride

Starting from 1.60 g (0.005 mol) of 2-amino-2-di-n-propylamino-tetraline-dihydrochloride (Example 4.5.1) the title compound is obtained analogously to Example 4.8.1 using propionylchloride in the form of the base which is converted into the hydrochloride analogously to Example 4.1.1. Yield 1.27 g (74.7% of theory), melting point 221° C. Recrystallisation from methanol/ether increases the melting point to 228° C.

Example 4.8.4

5-Chloroacetylamino-2-di-n-propylamino-tetralinehydrochloride

Starting from 1.60 g (0.005 mol) of 2-amino-2-di-n-propylamino-tetraline-dihydrochloride (Example 4.5.1) the title compound is obtained analogously to Example 4.8.1 using chloroacetylchloride in the form of the base which is converted into the hydrochloride analogously to Example 4.1.1. Yield 1.10 g (61.1% of theory), melting point 241° C. Recrystallisation from methanol/ether increases the melting point to 243° C.

Example 4.8.5

2-Di-n-propylamino-5-(trifluoroacetylamino)-tetralinehydrochloride

Starting from 1.60 g (0.005 mol) of 2-amino-2-di-n-propylamino-tetraline-dihydrochloride (Example 4.5.1) the title compound is obtained analogously to Example 4.8.1 using trifluoroacetic anhydride in the form of the base which is crystallised as the hydrochloride analogously to Example 4.1.1. Yield 0.70 g (37.0% of theory), melting point 233° C., unchanged after recrystallisation from methanol/ether.

Example 4.8.6

5-Benzoylamino-2-di-n-propylamino-tetraline

Starting from 3.19 g (0.01 mol) of 5-amino-2-di-n-propylamino-tetraline-dihydrochloride (Example 4.5.1) the title compound (3.6 g of crude product) is obtained analogously to Example 4.8.1 using benzoylchloride and is crystallised from diethylether/petroleum ether. Yield 2.8 g (79.9% of theory), melting point 97° C.

Example 4.8.7

2-Di-n-propylamino-5-formylamino-tetraline-hydrochloride 1.23 g (0.005 mol) of 5-amino-2-di-n-propylaminotetraline, base, (Example 4.5.1) are refluxed with 2.65 g (0.058 mol) of formic acid and 5.60 g of acetic anhydride (0.055 mol) for 2 hours. The reaction mixture is then poured into 50 ml of ice water and mixed with 15 ml of conc. ammonia. The base which is separated is extracted three times with methylene chloride (25, 15, 15 ml) and the combined extracts are washed with water, dried with sodium sulphate and concentrated by rotary evaporation, after the drying agent has been filtered off, finally at 80° C. under a complete water-jet vacuum. The residue, consisting of the base of the title compound, is converted analogously to Example 4.1.1 into the hydrochloride which is obtained in a yield of 1.15 g (74.0% of theory) and with a melting point of 250° C.

Example 4.8.8

2-Di-n-propylamino-5-methoxycarbonylamino-tetralinehydrochloride

Starting from 1.60 g (0.005 mol) of 5-amino-2-di-n-propylamino-tetraline-dihydrochloride (Example 4.5.1) the title compound is obtained in the form of the base analogously to Example 4.8.1 using methylchloroformate. This base is purified by column chromatography on 130 g of silica gel using methylene chloride/methanol/conc. ammonia 90:10:0.5 as eluant and then crystallised as the hydrochloride analogously to Example 4.1.1. Yield 1.0 g (58.8% of theory, melting point 220°

C., unchanged after recrystallisation from methanol/ether.

Example 4.8.9

5-(Carbamoylamino)-2-di-n-propylamino-tetralinehydrochloride 1.60 g (0.005 mol) of 5-amino-di-n-propylaminotetraline-hydrochloride (Example 4.5.1) are dissolved in 20 ml of water and the solution is heated to 80° C. for 15 minutes after the addition of 1.10 g (0.013 mol) of potassium cyanate. After cooling, the mixture is made ammoniacal with conc. ammonia and extracted three times with ethyl acetate. The combined extracts are washed with water, dried with sodium sulphate and concentrated by rotary evaporation, finally at 80° C. and under a complete water-jet vacuum. The title compound is obtained in the form of the base which is purified by chromatography analogously to Example 4.8.8 and crystallised as the hydrochloride. Yield 1.12 g (68.7% of theory), melting point 265° C., unchanged after recrystallisation from methanol/ether.

4.9 Compounds (12) and (9) from (17) and (7), respectively

Example 4.9.1

2,5-Di-(n-propylamino)-tetraline-dihydrochloride (a) 5-Acetylamino-2-propionylamino-tetraline Starting from 12.3 g (0.06 mol) of 5-acetylamino-2-amino-tetraline (known substance prepared by debenzylation of 5-acetylamino-2-benzylamino-tetraline (Example 4.1.16) analogously to Example 4.4.1) the title compound is obtained by propionylation analogously to Example 4.5.1 a) in a yield of 13.5 g (86.3% of theory).

(b) 5-Amino-2-propionylamino-tetraline

Starting from 13.5 g (0.052 mol) of 5-acetylamino-2-propionylamino-tetraline (see above) the title compound is obtained by selective cleavage of the N-acetyl group analogously to Example 4.5.1 b) in a yield of 7.9 g (69.8% of theory).

(c) 2,5-Di-(propionylamino)-tetraline

Starting from 0.87 g (0.004 mol) of 5-amino-2-propionylamino-tetraline (see above) the title compound is obtained by propionylation analogously to Example 4.5.1 a) in a yield of 0.98 g (89.9% of theory) and with a melting point of 270° C.

(d) 2,5-Di-(n-propylamino)-tetraline-dihydrochloride

Starting from 0.82 g (0.003 mol) of 2,5-di(propionylamino)-tetraline (see above) the base of the title compound is first obtained by reduction with lithium aluminium hydride (0.46 g, 0.012 mol) analogously to Example 4.5.1 c). This base is purified by column chromatography on 70 g of silica gel using methylene chloride/methanol/ammonia 90:10:0.5 and crystallised as the dihydrochloride. Yield 0.42 g (43.8% of theory), melting point 234° C., unchanged after recrystallisation from ethanol/ether.

Example 4.9.2

5-n-Butylamino-2-n-propylamino-tetraline-dihydrochloride

Starting from 0.87 g (0.004 mol) of 5-amino-2-propionylamino-tetraline, the title compound is obtained via the intermediate product 5-butyroylamino-2-propionylamino-tetraline analogously to Example 4.9.1 c) and d) in a total yield of 0.49 g (36.8% of theory) and with a melting point of 256° C. which does not change after recrystallisation from ethanol/ether.

Example 4.9.3

5-Benzylamino-2-n-propylamino-tetraline-dihydrochloride

Starting from 2.60 g (0.012 mol) of 5-amino-2-propionylamino-tetraline, the title compound is obtained via the intermediate product 5-benzylamino-2-propionylamino-tetraline analogously to Example 4.9.1 c) and d) in a total yield of 2.01 g (44.7% of theory) and with a melting point of 259° C. which does not change after recrystallisation from ethanol/ether.

Example 4.9.4

5-(2-Phenylethyl-amino)-2-n-propylamino-tetralinedihydrochloride

Starting from 0.87 g (0.004 mol) of 5-amino-2-propionylamino-tetraline analogously to Example 4.9.1 c) and d) the title compound is obtained in a total yield of 0.55 g (35.1% of theory) and with a melting point of 245° C. which does not change after recrystallisation from methanol/ether.

Example 4.9.5

5-(3-Phenylpropyl-amino)-2-n-propylamino-tetralinedihydrobromide

Starting from 0.87 g (0.004 mol) of 5-amino-2-propionylamino-tetraline the title compound is obtained via the intermediate product 5-(3-phenylpropionyl-amino-2-propionylamino-tetraline analogously to Example 4.9.1 c) and d) in a total yield of 0.124 g (6.4% of theory) and with a melting point of 195° C.

Example 4.9.6

2-Di-n-propylamino-5-ethylamino-tetraline-hydrochloride

Starting from 28.3 g (0.10 mol) of 5-acetylamino-2-(N-propionyl-N-n-propyl-amino)-tetraline (Example 4.5.1 a)) the title compound is obtained, initially in the form of the base, by reduction with 12.5 g (0.33 mol) of lithium aluminium hydride analogously to Example 4.9.1 d), in a yield of 20.1 g (73.2% of theory). The base could not be crystallised either as it was or as a dihydrochloride. However, a sample crystallised as a monohydride from ethanol/ether. Melting point 187° C., unchanged after recrystallisation from ethanol/ether.

4.10 Compounds (12) and (9) from (16) and (10), respectively

Example 4.10.1

5-Methylamino-2-n-propylamino-tetraline-dihydrochloride 0.50 g (1.92 mmol) of 5-(N-acetyl-N-methyl-amino)-2-n-propylamino-tetraline-hydrochloride (Example 4.7.8) are stirred with 12.5 g (0.22 mol) of potassium hydroxide in 40 ml of diethyleneglycol for 24 hours at 150° C. The mixture is then cooled, diluted with 400 ml of water and extracted three times with ethyl acetate (50, 15 and 15 ml). The combined extracts are washed with 20 ml of water, dried with sodium sulphate and, after the drying agent has been filtered off, concentrated by rotary evaporation, finally at 80° C. under a complete water-jet vacuum. The residue is crystallised as the hydrochloride analogously to Example 4.1.1. The title compound is obtained in a yield of 0.39 g (69.7% of theory) and with a melting point of 245° C. which does not change when recrystallised from ethanol/ether.

Example 4.10.2

5-Propargylamino-2-n-propylamino-tetralinedihydrochloride 0.48 g (0.0015 mol) of 5-(N-acetyl-N-propargylamino)-2-n-propylamino-tetraline-hydrochloride (Example 4.7.11) are refluxed in 10 ml of ethanol and 30 ml of 6 N hydrochloric acid for 16 hours. The mixture is then concentrated by rotary evaporation, finally at 80° C. under a complete water-jet vacuum. The residue is shaken with 50 ml of water, 50 ml of methylene chloride and excess ammonia. The aqueous phase separated off is extracted twice more with 15 ml of methylene chloride. The combined methylene chloride extracts are washed with 20 ml of water and concentrated by rotary evaporation as described above. The residue is crystallised analogously to Example 4.1.1 in the form of the dihydrochloride. Yield 0.12 g (25.2% of theory), melting point 198° C., unchanged after recrystallisation from ethanol/ether.

4.11 Compounds (11) from (10)

Example 4.11.1

2-Di-n-propylamino-5-(N-ethyl-N-methyl-amino)-tetralinedihydrochloride 1.1 g (3.63 mmol) of 5-(N-acetyl-N-methyl-amino)-2-dimethylamino-tetraline (Example 4.7.1) are reduced with 0.49 g (0.013 mol) of lithium aluminium hydride analogously to Example 4.5.1 c). The base of the title compound obtained is purified by column chromatography on 100 g of silica gel with methylene chloride/methanol/conc. ammonia 95:5:0.1 and crystallised as the dihydrochloride analogously to Example 4.1.1. Yield 0.47 g (35.8% of theory), melting point 169° C., unchanged after recrystallisation from methanol/ether.

Example 4.11.2

5-Diethylamino-2-di-n-propylamino-tetralinedihydrochloride

Starting from 2.20 g (0.00695 mol) of 5-(N-acetyl-N-ethylamino)-2-di-n-propylamino-tetraline (Example 4.7.2) the title compound is obtained analogously to Example 4.11.1 in a yield of 1.40 g (53.6% of theory) and with a melting point of 213° C. which does not change after recrystallisation from methanol/ether.

Example 4.11.3

5-(N-Ethyl-N-methyl amino)-2-n-propylamino-tetralinedihydrochloride

Starting from 0.56 g (1.89 mmol) of 5-(N-acetyl-N-methyl-amino)-2-n-propylamino-tetraline-hydrochloride (Example 4.7.8) which is converted into the base, the title compound is obtained as a base by reduction in 20 ml of absolute tetrahydrofuran analogously to Example 4.5.1 c), but using 1.90 ml of 2-molar diboran solution in tetrahydrofuran (THF) as reducing agent. The base is purified by column chromatography (50 g of silica gel, methylene chloride/methanol/conc. ammonia 90:10:0.5) and crystallised as the dihydrochloride analogously to Example 4.1.1, in a yield of 0.33 g (54.6% of theory) and with a melting point of 200° C.

Example 4.11.4

5-Diethylamino-2-n-propylamino-tetraline-dihydrochloride

Starting from 1.03 g (0.0033 mol) of 5-(N-acetyl-N-ethylamino)-2-n-propylamino-tetraline-hydrochloride (Example 4.7.8) which is converted into the base, the title compound is obtained in base form by reduction in 30 ml of absolute tetrahydrofuran analogously to Example 4.5.1 c), but using 3.3 ml of 2-molar diborandimethylsulphide complex solution in tetrahydrofuran as the reducing agent. This base is purified by filtering over 16 g of aluminium oxide (activity stage III, neutral) using methylene chloride as solvent and is crystallised analogously to Example 4.1.1 in the form of the dihydrochloride which is obtained in a yield of 0.54 g (49.1%) and with a melting point of 201° C.

4.12 Compounds (9) from (11)

Example 4.12.1

2-Di-n-propylamino-5-methylamino-tetraline-hydrochloride (a)

5-(N-Benzoyl-N-methyl-amino)-2-di-n-propylaminotetraline

Starting from 3.50 g (0.010 mol) of 5-benzoylamino-2-di-n-propylamino-tetraline (Example 4.8.6) the title compound is obtained by methylation analogously to Example 4.7.1 in a yield of 3.30 g (90.5%).

(b)

5-(N-Benzyl-N-methyl-amino)-2-di-n-propylaminotetraline

The title compound is obtained by reduction of 5-(N-benzoyl-N-methyl-amino)-2-di-n-propylamino-tetraline (see above) with diborane analogously to Example 4.11.4.

(c)

2-Di-n-propylamino-5-methylamino-tetralinehydrochloride

The title compound is obtained in the form of the base by catalytic debenzylation of 5-(N-benzyl-N-methyl)-2-di-n-propylamino-tetraline (see above) analogously to Example 4.4.1. The base is converted into the monohydrochloride analogously to Example 4.1.1. Total yield over 3 reaction steps 1.2 g (40.4% of theory), melting point 218° C., unchanged after recrystallisation from ethanol/ether.

4.13 Enantiomerically pure compounds

Example 4.13.1

(R/S)- and (R/R)-5-Acetylamino-2-(1-phenylethylamino)tetraline (a) 5-Acetylamino-2-(1-phenylethylamino)-tetraline (mixture of diastereoisomers)

Starting from 16.24 g (0.08 mol) of 5-acetylamino-2-tetralone, 240 ml of methanol, 19.0 g (0.12 mol) of (R)-1-phenylethylamine-hydrochloride and 6.0 g (0.096 mol) of sodium cyanoborohydride, the title compound is obtained analogously to Example 4.1.11 and is crystallised from 75 ml of toluene. Yield 18.5 g (74.9% of theory), melting point 158° C. It consists of approximately equal parts of the (R/R)- and (S/R)-diastereoisomers.

(b)
(R/S)-5-Acetylamino-2-(1-phenylethylamino)-tetraline
(D-mandelate and free base)

18.5 g (0.060 mol) of the mixture of diastereoisomers (see above) are dissolved in 300 ml of acetonitrile with 9.13 g (0.060 mol) of D-mandelic acid. When the solution is left to stand at ambient temperature for 24 hours a crystalline fraction is obtained in which the (R/S)-form is concentrated (10.6 g). Recrystallisation from 115 ml of acetonitrile yields 8.65 g of purified (R/S)-form with a melting point of 165° C.

The crystallised D-mandelate of the (R/S) form (8.65 g) is converted using water, methylene chloride and excess ammonia in the usual way, into the (R/S) base which is obtained as the evaporation residue of the methylene chloride extracts. When it is treated with diethylether, crystallisation occurs. The crystallised (R/S) base (5.8 g, 31.3% of theory) melts at 111° C. and has a specific rotation of $[\alpha]_D^{20} = +29.8°$ (c=1, 1 N HCl/methanol 1:1).

(c)
(R/R)-5-Acetylamino-2-(1-phenylethylamino)-tetraline

The combined mother liquors from the separation of the (R/S) mandelates (see above) are concentrated by evaporation and the residue is converted with water, methylene chloride and excess ammonia in the usual way into the base form which is obtained as the evaporation residue of the methylene chloride extracts. This residue is crystallised from 100 ml of ethyl acetate. Further recrystallisation from 10 times the quantity of ethyl acetate yields 4.7 g (25.4% of theory) of pure (R/R) base with a melting point of 141° C. and a specific rotation of $[\alpha]_D^{20} = +145.3°$ (c=1, 1 N HCl/methanol 1:1).

The (R/S) and (R/R) diastereoisomers can also be separated as bases by column chromatography on silica gel using methylene chloride/methanol/ammonia 90:10:0.5 as eluant, the (R/S) form being eluted first.

Example 4.13.2

(−)-(S)-5-Acetylamino-2-amino-tetraline-hydrochloride 3.20 g (0.0104 mol) of (R/S)-5-acetylamino-2-(1-phenylethylamino)-tetraline (Example 4.13.1 b) are hydrogenated in 70 ml of methanol in the presence of 0.7 g of 10% palladium/charcoal at 20° to 60° C. analogously to Example 4.4.1. The title compound is obtained in a yield of 2.00 g (79.9% of theory), melting point 310° C., specific rotation $[\alpha]_D^{20} = -50.0°$ (c=1, 1 N HCl/methanol 1:1).

Example 4.13.3

(+)-(R)-5-Acetylamino-2-amino-tetraline-hydrochloride

Starting from 2.80 g (0.0091 mol) of (R/R)-5-acetylamino-2-(1-phenyl-ethylamino)-tetraline (Example 4.13.1 c) the title compound is obtained analogously to Example 4.2.1 in a yield of 1.8 g (82.2% of theory) melting point 311° C., specific rotation $[\alpha]_D^{20} = +50.2°$ (c=1, 1 N HCl/methanol 1:1).

Example 4.13.4

(−)-(S)-2,5-Diamino-tetraline-dihydrochloride

Starting from 0.20 g (0.832 mmol) of (−)-(S)-5-acetylamino-2-amino-tetraline-hydrochloride (Example 4.13.2) the title compound is obtained analogously to Example 4.2.1 in a yield of 0.19 g (98.1% of theory) and with a melting point of >320° C. $[\alpha]_D^{20} = -60.2°$ (c=1, 1 N HCl/methanol 1:1).

Example 4.13.5

(+)-(R)-2,5-Diamino-tetraline-dihydrochloride

Starting from 0.20 g (0.832 mmol) of (+)-(R)-5-acetylamino-2-amino-tetraline-hydrochloride (Example 4.13.3) the title compound is obtained analogously to Example 4.2.1 in a yield of 0.19 g (98.1% of theory) and with a melting point of >320° C. $[\alpha]_D^{20} = -60.1°$ (c=1, 1 N HCl/methanol 1:1).

Example 4.13.6

(−)-(S)-5-Amino-2-n-propylamino-tetralinedihydrochloride

The title compound is obtained analogously to the Examples for the racemic form. Melting point >300° C., $[\alpha]_D^{20} = -56.3°$ (c=1, 1 N HCl/methanol 1:1)

Example 4.13.7

(+)-(R)-5-Amino-2-n-propylamino-tetralinedihydrochloride

The title compound is obtained analogously to the Examples for the racemic form. Melting point >300° C., $[\alpha]_D^{20} = -56.2°$ (c=1, 1 N HCl/methanol 1:1)

Example 4.13.8

(−)-(S) 5-Acetylamino-2-di-n-propylamino-tetralinehydrochloride

The title compound is obtained analogously to the Examples for the racemic form. Melting point 236° C., $[\alpha]_D^{20} = -42.9°$ (c=1, 1 N HCl/methanol 1:1)

Example 4.13.9

(+)-(R)-5-Acetylamino-2-di-n-propylamino-tetralinehydrochloride

The title compound is obtained analogously to the Examples for the racemic form. Melting point 236° C., $[\alpha]_D^{20} = +43.1°$ (c=1, 1 N HCl/methanol 1:1)

Example 4.13.10

(−)-(S)-5-Amino-2-di-n-propylamino-tetralinedihydrochloride

The title compound is obtained analogously to the Examples for the racemic form. Melting point 278° C., $[\alpha]_D^{20} = -52.9°$ (c=1, 1 N HCl/methanol 1:1)

Example 4.13.11

(+)-(R)-5-Amino-2-di-n-propylamino-tetralinedihydrochloride

The title compound is obtained analogously to the Examples for the racemic form. Melting point 278° C., $[\alpha]_D^{20} = +54.8°$ (c=1, 1 N HCl/methanol 1:1).

What is claimed is:

1. A method for treating disorders of the dopaminergic systems treatable by an agent having dopamine-agonizing activity, in a patient, which comprises administering to the patient a compound of the formula:

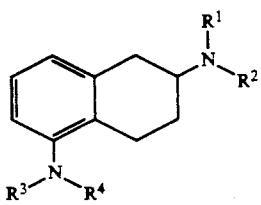

wherein
R¹ represents hydrogen, $C_{1-12}$ alkyl, $C_{3-12}$ alkenyl, $C_{3-12}$ alkynyl, —$(CH_2)_a$-cycloalkyl, or aralkyl wherein a represents one of the numbers 1,2,3,4,5,6,7,8,9,10,11,12;

R² represents $C_{1-12}$ alkyl, $C_{1-12}$ alkyl, $C_{3-12}$ alkenyl, $C_{3-12}$ alkynyl, —$(CH_2)_b$-cycloalkyl,

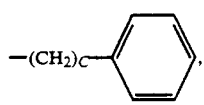

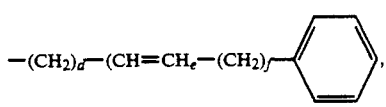

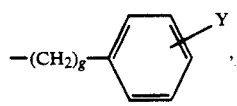

—$(CH_2)_h$-heteroaryl, or acyl wherein
b represents one of the numbers 1,2,3,4,5,6,7,8,9,10,11 or 12,
c represents one of the numbers 1,2,3,4,5,6,7,8,9,10,11 or 12,
d represents one of the numbers 1,2,3,4,5 or 6,
e represents one of the numbers 1,2 or 3,
f represents one of the numbers 0,1,2,3 or 4,
g represents one of the numbers 1,2,3,4,5 or 6,
h represents one of the numbers, 1,2,3,4,5,6,7,8,9,10, 11,12,13,14,15,16,17,18,19 or 20,
Y represents $C_{1-12}$ alkyl, halogen, alkoxy or hydroxy;
R³ represents hydrogen, $C_{1-12}$ alkyl, $C_{3-12}$ alkenyl, $C_{3-12}$ alkynyl, —$(CH_2)_i$-cycloalky, aralkyl, formyl, acyl, alkylcarbonyl, alkyloxycarbonyl, or

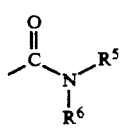

wherein
R⁵ represents alkyl,
R⁶ represents alkyl,
R⁵ and R⁶ together with the nitrogen atom can represent a heterocyclic group which can contain another heteroatom, and
i represents one of the numbers 1,2,3,4,5,6,7,8,9,10,11 or 12;
R⁴ represents hydrogen of $C_{1-12}$ alkyl; or the acid addition salts thereof, in an amount to exert a therapeutically effective dopamine-agonizing effect.

2. A method as recited in claim 1 wherein
R¹ represents hydrogen, $C_{1-6}$ alkyl, $C_{3-6}$ alkenyl, $C_{3-6}$ alkynyl, —$(CH_2)_a$-cycloalkyl, or aralkyl with 1 to 6 carbon atoms in the aliphatic part, wherein a represents one of the numbers 1,2,3,4,5 or 6;
R² represents $C_{1-6}$ alkyl, $C_{3-6}$ alkenyl, $C_{3-6}$ alkynyl, —$(CH_2)_b$-cycloalkyl,

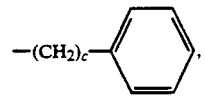

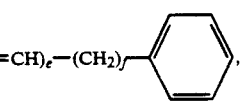

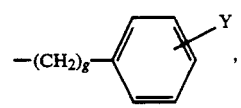

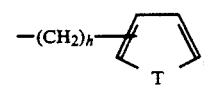

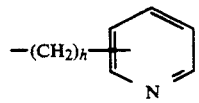

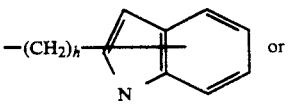

acyl, wherein
b represents one of the numbers 1,2,3,4,5 or 6,
c represents one of the numbers 1,2,3,4,5,6,7,8,9 or 10,
d represents one of the numbers 1,2 or 3,
e represents one of the numbers 1 or 2,
f represents one of the numbers 0, 1 or 2,
g represents one of the numbers 1,2,3 or 4,
h represents one of the numbers 1,2,3,4,5,6,7,8,9,10,12,13 or 14,
Y represents $C_{1-16}$ alkyl, halogen, lower alkoxy or hydroxy, and
T represents oxygen, sulphur or nitrogen;
R³ represents hydrogen, $C_{1-6}$ alkyl, $C_{3-6}$ alkenyl, $C_{3-6}$ alkynyl, —$(CH_2)_i$-cycloalkyl, phenylalkyl, formyl, aryl, alkylcarbonyl, alkoxycarbonyl, or

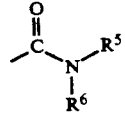

wherein
R⁵ represents lower alkyl,
R⁶ represents lower alkyl,
R⁵ and R⁶ together with the nitrogen atom can form a heterocyclic group which can contain a further heteroatom, and i represents one of the numbers 1,2,3,4,5 or 6; and
R⁴ represents hydrogen or lower alkyl.

3. A method as recited in claim 1 wherein
R¹ represents hydrogen, methyl, ethyl, propyl, allyl, propargyl, cyclopropylmethyl or benzyl;
R² represents methyl, ethyl, propyl, allyl, propargyl, cyclopropylmethyl,

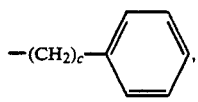

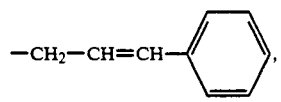

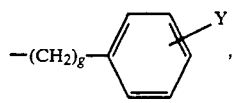

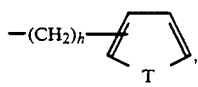

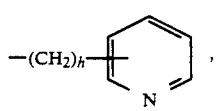

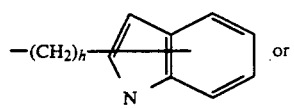

acyl wherein
c represents one of the numbers 1,2,3,4,5,6,7,8 or 9,
g represents one of the numbers 2 or 3,
h represents one of the numbers 1,2,3,4,5,6,7,8,9,10,11 or 12,
Y represents methyl, fluorine, chlorine, bromine, methoxy, or hydroxy, and
T represents oxygen or sulphur;
R³ represents hydrogen, methyl, ethyl propyl, allyl, propargyl, cyclopropylmethyl, benzyl, phenylethyl, phenylpropyl, formyl, acyl, methylcarbonyl, ethylcarbonyl, trifluoromethylcarbonyl, methoxycarbonyl or aminocarbonyl; and
R⁴ represents hydrogen, methyl, ethyl, n-propyl or isopropyl.

4. A method as recited in claim 1 wherein the compound is (+)-or (−)-5-amino-2-[N-(3-phenylpropyl)-N-n-propylamino]-tetraline.

5. A method as recited in claim 1 wherein the compound is (+)-or (−)-5-amino-2-[N-(3-phenylpropyl)-N-n-propyl-amino]-tetraline.

6. A method as recited in claim 1 wherein the compound is (+)-or (−)-5-amino-2-[N-(4-phenylbutyl)-amino]-tetraline.

7. A method as recited in claim 1 wherein the compound is (+)-or (−)-5-amino-2-[N-(4-phenylbutyl)-N-n-propyl-amino]-tetraline.

* * * * *